United States Patent
Jermy et al.

(10) Patent No.: US 11,160,763 B2
(45) Date of Patent: Nov. 2, 2021

(54) MULTIFUNCTIONAL PH RESPONSIVE DRUG DELIVERY SYSTEM AND METHOD OF USE

(71) Applicant: Imam Abulrahman Bin Faisal University, Dammam (SA)

(72) Inventors: Balasamy Rabindran Jermy, Dammam (SA); Vijaya Ravinayagam, Dammam (SA)

(73) Assignee: Imam Abulrahman Bin Faisal University, Dammam (SA)

( * ) Notice: Subject to any disclaimer, the term of this patent is extended or adjusted under 35 U.S.C. 154(b) by 0 days.

(21) Appl. No.: 16/295,655

(22) Filed: Mar. 7, 2019

(65) Prior Publication Data

US 2020/0281864 A1    Sep. 10, 2020

(51) Int. Cl.
| | | |
|---|---|---|
| A61K 9/51 | (2006.01) | |
| A61K 33/243 | (2019.01) | |
| A61K 41/00 | (2020.01) | |
| A61P 35/00 | (2006.01) | |

(52) U.S. Cl.
CPC .......... *A61K 9/5115* (2013.01); *A61K 9/5138* (2013.01); *A61K 9/5146* (2013.01); *A61K 9/5153* (2013.01); *A61K 9/5161* (2013.01); *A61K 33/243* (2019.01); *A61K 41/00* (2013.01); *A61P 35/00* (2018.01)

(58) Field of Classification Search
CPC .. A61K 9/5115; A61K 9/5161; A61K 9/5138; A61K 33/243; A61K 9/5153; A61K 41/00; A61K 9/5146; A61P 35/00
See application file for complete search history.

(56) References Cited

FOREIGN PATENT DOCUMENTS

| | | |
|---|---|---|
| CN | 104225599 B | 5/2017 |
| EP | 2 111 881 A1 | 10/2009 |
| WO | 2018/140304 A1 | 8/2018 |

OTHER PUBLICATIONS

Ulbrich et al. (Chemical Reviews (2016), 116, 5338-5431).*
Liu et al.(Langmuir 2011, 27, 3095-3099).*
Arande et al. (Journal of Nanomaterials (2012), Article ID 816496, 10 pages).*
Munoz et al. Int. J. Mol. Sci. (2010), 11, 3069-3086.*
Sharifabad (Thesis: Study of Porous Nanocomposites for Bio-Catalysis and Drug Delivery (2016).*
Jermy, et al. ; Hierarchical mesosilicalite nanoformulation integrated with cisplatin exhibits target-specific efficient anticancer activity ; Springer Nature Switzerland AG ; 2017 ; Abstract Only ; 11 Pages.
Liao ; Developing a Silica-Coated Iron Oxide Nanovehicle for Antibody-Targeted Cancer Therapy ; Wellesley Colege Digital Scholarship and Archive, Honors Thesis Collection ; 2015 ; 60 Pages.
Vallet-Regi, et al. ; Mesoporous Silica Nanoparticles for Drug Delivery: Current Insights ; MDPI Molecules ; Dec. 25, 2017 ; 19 Pages.

* cited by examiner

*Primary Examiner* — Shirley V Gembeh
(74) *Attorney, Agent, or Firm* — Oblon, McClelland, Maier & Neustadt, L.L.P.

(57) ABSTRACT

A multi-functional drug composition capable of pH responsive drug release comprising siliceous nanoparticles having three dimensional cage structures type silica with thick pore walls and mesosilicalite, superparamagnetic iron oxide nanoparticles (SPION) and pharmaceutical composition thereof is disclosed. The drug delivery system is useful for targeting a drug to particular diseased tissues such as cancerous tissues.

7 Claims, 18 Drawing Sheets

MULTIFUNCTIONAL PH RESPONSIVE DRUG DELIVERY SYSTEM AND METHOD OF USE

BACKGROUND OF THE INVENTION

Field of the Disclosure

This disclosure relates to a multi-functional drug composition capable of pH responsive drug release, and methods for treating, imaging and/or diagnosing tumors. The system can include a functionalized porous silica carrier loaded with superparamagnetic iron nanoparticles (SPIONs) and a drug and/or pharmaceutical composition.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Platinum(II) complexes, in particular, cisplatin are among the most effective anticancer drugs as they have excellent cytotoxic activities. These anticancer drugs, however, suffer from several drawbacks. Cancers treated with platinum(II) complexes develop drug resistance, and the patients suffer from undesirable side effects including peripheral neuropathy, nephrotoxicity, hearing loss, nausea, and associated pain. Although some platinum(II) complexes such as carboplatin and oxaliplatin have reduced toxicity with reasonable anticancer activity, the replacement of chloride ligands of cisplatin decreases the chemotherapeutic efficacy of the platinum(II) complex leading to the use of larger doses, and hence significantly increases the cost of treatment [Jung et al. "Direct Cellular Responses to Platinum-Induced DNA Damage" *Chemical Reviews* 2007, 107, 1387-1407]. Many attempts to identify cisplatin analogs having the desired clinical efficacy while avoiding or minimizing the side effects have failed [Eckardt et al. "Phase II study of picoplatin as second-line therapy for patients with small-cell lung cancer" *J. Clin. Oncol.* 2009, 27, 2046-2051]. The drug formulations associated with the use of cisplatin associated are reported to have a major role in determining the cytotoxicity of the cisplatin. Dimethyl sulfoxide (DMSO) deactivates the anticancer activity of cisplatin due to platinum complexation with the solvent, whereas dimethylformamide (DMF) enhances the cytotoxicity of cisplatin [Hall et al. "Dimethyl sulfoxide Inactivates Cisplatin, Carboplatin and Other Platinum Complexes. *Cancer Res.* 2014, 74(14), 3913-3922].

Nanocarriers have been shown to reduce the side effects of anticancer drugs by selectively targeting tumors through enhanced permeability and retention at the tumor site thereby reducing the effective dose of the drug and minimizing the exposure of normal cells to the cytotoxic effects of the drug. Numerous types of nanocarriers for cisplatin loading including polymer based micelles of different chain lengths and nanofibers have been studied. For instance, cisplatin formulations containing epidermal growth factor and loaded onto polyethylene glycol-polylactic-co-glycolic acid-polylysine through double emulsion was shown to have reduced the toxicity and enhanced anticancer activity in a human ovarian adenocarcinoma cell line [Wang et al. Toxicity and therapy of cisplatin-loaded EGF modified mPEG-PLGA-PLL nanoparticles for SKOV3 cancer in mice, *Biomaterials* 2013, 34, 4068-4077]. Nanofibers with high textural characteristics such as high surface area, strong bio-adhesiveness, and high loading capabilities are reported to be effective for cisplatin loading. In a multistep synthesis protocol, preparation of a polymeric solution containing polycaprolactone, dichloromethane, DMF and chitosan was reported. Dissolution in DMF using electrospinning was shown to be effective for cisplatin loading in poly(lactic-co-glycolic acid) (PLGA) nanoparticles [Parhizkar et al. "Electrohydrodynamic encapsulation of cisplatin in poly (lactic-co-glycolic acid) nanoparticles for controlled drug delivery" *Nanomedicine: Nanotechnology, Biology, and Medicine* 2016, 12, 1919-1929]. The PLGA composition was effective for encapsulating 70 wt. % of cisplatin and loaded up to 10 wt. % of cisplatin using dimethylacetamide solvent and electrohydrodynamic atomization (electro spray) technique with electric potential voltage of 12-20 kV. Other effective polymeric carriers of cisplatin have been reported. However, developing a large scale production method for such nanomedicine compositions requires a multiplicity of steps, the usage of several solvents, and difficulties with the stability of the polymeric template.

Nanoporous silica based drug delivery systems have attracted interest as drug carriers. In comparison to other drug carriers such as capsules, viruses and liposomes, the nanosilica is biocompatible and stable in biological environments. Mesosilica nanoparticles with surface carboxyl groups bind oxaliplatin. The oxiplatin bound to mesosilica displayed high cytotoxicity against a HepG2 cell line [He et al. "Synthesis porous silica nanoparticle-oxaliplatin conjugates for improved anticancer drug delivery" *Colloids and Surfaces B: Biointerfaces* 2014, 117, 75-81]. The synthesis of hollow type mesoporous silica functionalized with carboxyl groups was reported as an efficient drug delivery platform for cisplatin. Carboxylic group functionalized hollow mesoporous silica nanospheres were synthesized in the presence of polystyrene spheres templates having large surface area for loading cisplatin (~48%) [Farsangi et al. "One-pot controllable synthesis of carboxylic group functionalized hollow mesoporous silica nanospheres for efficient cisplatin delivery" Z. *RSC Adv.* 2016; 6, 67592-67598]. Mesoporous silica coordinated with the photosensitizer aluminum chloride phthalocyanine and cisplatin in DMSO was an effective anticancer agent for human cervical cancer therapy. In particular, a synergetic effect observed between the photosensitizer and cisplatin resulted in greater toxicity against HeLa cells in comparison to a cisplatin-silica combination [Vivero-Escoto et al. "Mesoporous Silica Nanoparticles Loaded with Cisplatin and Phthalocyanine for Combination Chemotherapy and Photodynamic Therapy in vitro" *Nanomaterials* 2015, 5, 2302-2316]. U.S. patent application Ser. No. 15/992,953—incorporated herein by reference in its entirety discloses a hierarchical mesosilicalite nanocarrier loaded with platinum (II) complexes, which is shown to be effective cytotoxic formulation against cancer cell lines.

A core shell super paramagnetic $Fe_3O_4$ based mesoporous silica functionalized with carboxylic functional group was reported to be effective for cisplatin loading and controlled release. The nanocomposite formed by condensation of a silica source with carboxyethylsilanetriol sodium followed by the addition of carboxyl functional groups was reported to encapsulate cisplatin in aqueous DMSO and have anticancer activity against cancer cell lines A549 and MCF-7 [Zhu et al. "Magnetic core-mesoporous shell nanocarriers with drug anchorages suspended in mesopore interior for cisplatin delivery" Micropore Mesopore Mat. 2014, 196, 115-121]. The reported MCM-41 based nanocarriers have an amorphous framework structure, where drug release is controlled by several factors including derivatization, pore size, and the constraint imposed on diffusion by the pore nanostructure [Shen et al. "Physical state and dissolution ibuprofen formulated by co-spray drying with mesoporous silica: effect of pore and particle size. *Int. J. Pharm.* 2011, 410, 188-195; and Saha et al. "Controlled release of antipyrine from mesoporous carbons, *Micropor and Mesopor. Mater.* 2014, 196, 327-334]. Pharmaceutical industrial scale up of a formulation with pure mesoporous MCM-41 phase was limited due poor hydrothermal and steam stability.

In recent years, various techniques have been applied to improve the stability of nanosilica and the accessibility of the pores of MCM-41. The synthesis of hierarchical porous silicalite materials using a zeolite seed based hexagonal mesophase with a top-down and bottom-up approach was described [U.S. patent application Ser. No. 15/478,794—incorporated herein by reference in its entirety, and Jermy, B. R. "Synthesis of hexagonal aluminosilicate from liquid-crystalline mesophase using zeolitic nanoclusters: bottom-up versus top-down approach, *J Porous Mater* 2017]. The top-down approach involved preparation of hierarchical porous materials by disintegrating a fully grown zeolite such as silicalite or ZSM-5 or other zeolites in presence of a mesotemplate, while the bottom-up approach involved building mesoporous materials through zeolitic seed solution derived from basic chemical ingredients. The presence of a crystalline framework in SiMCM-41 mesophase would be highly advantageous for multifunctional therapeutics. Hierarchically structured mesoporous silicas (ZSM-5/MCM-41) with zeolitic ZSM-5 and mesoporous MCM-41 interlinked domains have been reported as catalysts in the petrochemical industry and the use of primary or secondary zeolitic building units of nano zeolitic seeds has been reported to increase framework crystallinity of MCM-41 in the synthesis of gel [Odedairo et al. "Aromatic transformation over ZSM-/MCM-41 composites with adjustable porosity in fluidized bed reactor, *Catal. Sci. Technol.,* 2012, 2, 1275-1286; and Balasamy et al. Unique catalytic performance of mesoporous molecular sieves containing zeolite units in transformation of m-xylene"*Appl. Catal. A: Gen.* 2011, 409-410, 223-233].

The combination of therapeutic compounds with tumor imaging agents was reported to improve the treatment efficacy and limit side effects due to onsite drug delivery [C. Sun, J. S. H. Lee, M. Zhang, Magnetic nanoparticles in MR imaging and drug delivery, Advanced Drug Delivery Reviews 60 (2008) 1252-1265]. The role of magnetic nanosilica drug carrier includes providing a response to external magnetic fields to thereby assist in bioimaging, targeting, and further to carry a therapeutic agent to a specific diseased site for treatment. The use of super paramagnetic iron oxide nanoparticles is particularly advantageous because the U.S. FDA has approved the particles for clinical use.

It is therefore one objective of the present disclosure to provide a multipurpose nanocarrier system in a single platform (e.g., composition) for tumor imaging with drug delivery capability leading to enhanced effectiveness of the treatment while minimizing undesirable side effects.

SUMMARY OF THE INVENTION

A first aspect of the invention is directed to a multifunctional drug composition capable of pH responsive drug release, comprising a pharmaceutical agent, porous silica nanoparticles, superparamagnetic iron oxide nanoparticles (SPIONs) or a mixture of SPIONs and NiO nanoparticles, a silane functionalization agent, and a polymer, wherein the SPIONS are present in the pores of the porous silica nanoparticles and the nanoparticles are functionalized with silane functionalization agent, and wherein the functionalized silica nanoparticles containing the SPIONs are encapsulated with the polymer.

In a preferred embodiment, the porous silica nanoparticle is selected from the group consisting of structured siliceous SBA-16 and mesosilicalite.

In another preferred embodiment, a multi-functional drug composition capable of pH responsive drug release comprises SPIONs.

In another preferred embodiment, a multi-functional drug composition capable of pH responsive drug release comprises a mixture SPIONs and NiO nanoparticles.

In another preferred embodiment, the structured siliceous SBA-16 has a three dimensional silica cage structure with thick pore walls.

In another preferred embodiment, the porous silica nanoparticles have pore sizes in the range of 1 nm to 60 nm.

In another preferred embodiment, the porous silica nanoparticle has a surface area in the range of 400 to about 1400 $m^2/g$.

In another preferred embodiment, the porous silica nanoparticle has a pore volume in the range of 0.30-0.90 mL/g.

In another preferred embodiment, the pharmaceutical agent is an anticancer drug.

In a more preferred embodiment, the drug is a platinum (II) complex.

In a most preferred embodiment, the platinum(II) complex is selected from the group consisting of cisplatin, carboplatin, oxaliplatin, nedaplatin, triplatin tetranitrate, phenanthriplatin, picoplatin, and strataplatin.

In another preferred embodiment, the platinum(II) complex is present in amount in the range of 0.001 to 1.8 mmol/g of the total weight of the smart drug delivery system.

In another preferred embodiment, the alkyltrialkoxysilane compound is selected from the group consisting of (3-aminopropyl)triethoxysilane (APTES), 3-chloropropyl trimethoxysilane, N-[-3-(trimethoxysilyl)propyl]aniline, and triethylenetetramine.

In another preferred embodiment, the polymer is a biocompatible polymer selected from the group consisting of polyacrylic acid (PAA), chitosan, poly(D,L-lactide-co-glycolide), and polyethylene glycol.

A second aspect of the invention is directed to a method of making the multi-functional drug composition capable of pH responsive drug release, comprising:

impregnating a porous silica nanocarrier with SPIONs or a mixture of SPIONs and NiO nanoparticles, functionalizing the SPIONs or SPIONs and NiO nanoparticles impregnated porous silica nanocarrier with a silane compound, encapsulating the functionalized SPIONs or SPIONs and NiO nanoparticles impregnated porous silica nanocarrier with biocompatible polymer in organic solvent, mixing the encapsulating functionalized SPIONs or a mixture of SPIONs and NiO nanoparticles impregnated porous silica nanocarrier with biocompatible polymer and drug to form a mixture, separating the nanocarrier loaded with the drug.

In a preferred embodiment, the organic solvent is an aprotic polar solvent, preferably selected from the group consisting of dimethyl formamide, dimethyl sulfoxide, acetonitrile, acetone, tetrahydrofuran, and dioxane.

In another preferred embodiment, the mixture is heated at 140° C. for two hours.

A third aspect of the invention is directed to a pharmaceutical composition comprising the multi-functional drug composition capable of pH responsive drug release of the invention.

In a preferred embodiment, the pharmaceutical composition comprises a multi-functional drug composition capable of pH responsive drug release loaded with a platinum(II) complex selected from the group consisting of cisplatin, carboplatin, oxaliplatin, nedaplatin, triplatin tetranitrate, phenanthriplatin, picoplatin, strataplatin, and combination thereof.

In another preferred embodiment, the multi-functional drug composition capable of pH responsive drug release is further loaded with a platinum(II) complex and at least one or more drugs.

In another preferred embodiment, the pharmaceutical composition further comprises one or more carriers and/or excipients selected from the group consisting of a buffer, an inorganic salt, a fatty acid, a vegetable oil, a synthetic fatty ester, a surfactant, a sugar, a polymer, and combinations thereof.

A fourth aspect of the invention is directed to a method for treating a proliferative disorder, comprising:

administering to a subject in need of therapy an effective amount of the pharmaceutical composition of the invention.

In a preferred embodiment of the method, the proliferative disorder is a cancer selected from the group consisting of ovarian cancer, cervical cancer, testicular cancer, colon cancer, bladder cancer, breast cancer, non-small cell lung cancer, esophageal cancer, endometrial cancer, head and neck cancer, and an osteogenic sarcoma.

In another preferred embodiment of the method, the proliferative disorder is a tumor.

In another preferred embodiment of the method, the subject is a mammal.

In a more preferred embodiment of the method, the mammal is human

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
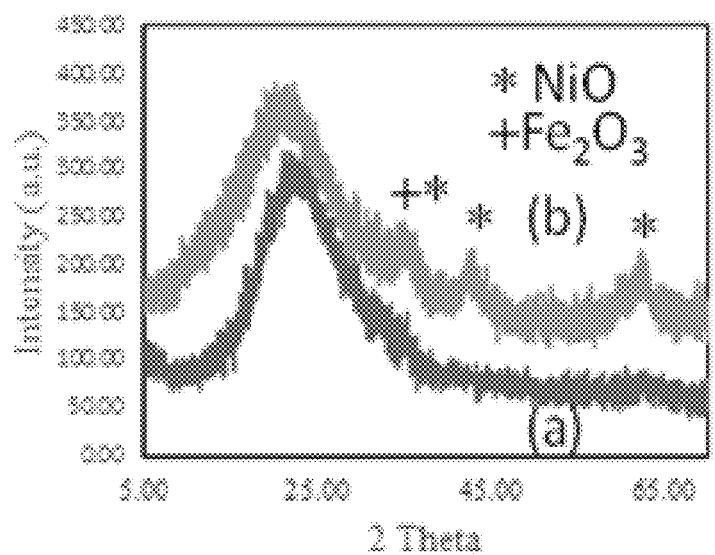
FIG. 1A shows XRD diffraction patterns (a) 10wtFe/S-16 (ND-95) and (b) 10wtFe10wtNi/S-16 (ND-91).

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

As used herein, the terms "compound" and "complex" are used interchangeably, and are intended to refer to a chemical entity, whether in a solid, liquid or gaseous phase, and whether in a crude mixture or purified and isolated.

Unless otherwise specified, "a" or "an" means "one or more".

As used herein, the term "salt" refers to derivatives of the disclosed compounds wherein the parent compound is modified by making acid or base salts thereof. Exemplary salts include, but are not limited to, mineral or organic acid salts of basic groups such as amines, and alkali or organic salts of acidic groups such as carboxylic acids. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

As used herein, the term "solvate" refers to a physical association of a compound, monomer or polymer of this disclosure with one or more solvent molecules, whether organic or inorganic. This physical association includes hydrogen bonding. In certain instances, the solvate will be capable of isolation, for example when one or more solvent molecules are incorporated in the crystal lattice of a crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvates include, but are not limited to, hydrates, ethanolates, methanolates, isopropanolates and mixtures thereof. Methods of solvation are generally known to those of ordinary skill in the art.

As used herein a "polymer" or "polymeric resin" refers to a large molecule or macromolecule, of many repeating subunits and/or substances composed of macromolecules. As used herein a "monomer" refers to a molecule or compound that may bind chemically to other molecules to form a polymer. As used herein the term "repeat unit" or "repeating unit" refers to a part of the polymer or resin whose repetition would produce the complete polymer chain (excluding the end groups) by linking the repeating units together successively along the chain. The method by which monomers combine end to end to form a polymer is referred to herein as "polymerization" or "polycondensation", monomers are molecules which can undergo polymerization, thereby contributing constitutional repeating units to the structures of a macromolecule or polymer. As used herein "resin" or "polymeric resin" refers to a solid or highly viscous substance or polymeric macromolecule containing polymers, preferably with reactive groups. As used herein a "copolymer" refers to a polymer derived from more than one species of monomer and are obtained by "copolymerization" of more than one species of monomer. Copolymers obtained by copolymerization of two monomer species may be termed bipolymers, those obtained from three monomers may be termed terpolymers and those obtained from four monomers may be termed quarterpolymers, etc. As used herein, "cross-linking", "cross-linked" or a "cross-link" refers to polymers and resins containing branches that connect polymer chains via bonds that link one polymer chain to another.

The cross-link may be an atom, a group of atoms, or a number of branch points connected by bonds, groups of atoms, or polymer chains. In the majority of cases, a cross-link is a covalent structure or covalent bond but the term may also describe sites of weaker chemical interactions, portion crystallites, and even physical interactions and entanglements. The cross-linking can alter the physical and mechanical properties of the polymer. Cross-linking may be formed by chemical reactions that are initiated by heat, pressure, change in pH, and/or radiation, with or without the presence of a cross-linking agent and/or catalyst. In certain embodiments, at least one diaminoalkane a cross-linking agent for the cross-linked polymeric resin described herein.

The following abbreviations are used throughout the text:

APTES: 3-Aminopropyl)triethoxysilane.

S-16: Siliceous SBA-16.

ND-43: 10 wt. % Iron oxide loaded over mesosilicalite, in situ designed silicalite-MCM-41 hierarchical porous material.

ND-90: 10 wt. % Iron oxide and 10 wt. % NiO impregnated over mesosilicalite, in situ designed silicalite-MCM-41 hierarchical porous material.

ND-87: Physical mixture of silicalite and MCM-41.

ND-88: 10 wt. % Iron oxide loaded over monodisperse hydrophilic spherical silica.

ND-89: 10 wt. % Iron oxide loaded over monodisperse hydrophobic spherical silica.

ND-91: 10 wt. % iron oxide and 10 wt % nickel oxide loaded over 3D cage type of structured siliceous SBA-16.

ND-92: Cisplatin loaded over 10 wt. % iron oxide loaded over mesocellular foam.

ND-95: 10 wt. % Iron oxide loaded over 3D cage type of structured siliceous SBA-16.

ND-97: 10 wt. % Iron oxide loaded over monodisperse hydrophilic spherical silica calcined at 750° C.

ND-100: Mesocellular foam functionalized with APTES and then loaded with cisplatin.

ND-101: Cisplatin functionalized over F127 (polymer) containing SiSBA-16.

ND108: (10wtFe/S-16-APTES): APTES functionalized over iron oxide loaded 3D cage type of structured siliceous SBA-16.

ND-116: Cisplatin conjugated with APTES functionalized over 10 wt. % iron oxide loaded 3D cage type of structured siliceous SBA-16.

ND-117: Nanocarrier containing cisplatin, APTES functionalized over 10 wt. % iron oxide loaded 3D cage type of structured siliceous SBA-16 wrapped with polyacrylic acid.

ND-124: Cisplatin conjugated with APTES functionalized over 10 wt % iron oxide loaded hydrophilic spherical silica.

Cp: cisplatin.

A first aspect of the invention is directed to a multifunctional drug composition capable of pH responsive drug release comprising a pharmaceutical agent, porous silica nanoparticles, superparamagnetic iron oxide nanoparticles (SPIONs) or a mixture of SPIONs and NiO nanoparticles, a silane functionalization agent, and optionally one or more polymer, wherein the SPIONS are present in the pores of the porous silica nanoparticles and the nanoparticles are functionalized with silane functionalization agent, and wherein the functionalized silica nanoparticles containing the SPIONs are optionally encapsulated with the polymer.

Any porous type silica, silicate or aluminosilicate may be used in the smart drug delivery system including, but not limited to, MCM-41, MCM-48, SBA-15, KIT-5, KIT-6, mesosilicalite, hierarchical porous silicalite and SBA-16. Methods of obtaining the various types porous silica are well-known in the art [see for example Gobin, Oliver Christian "SBA-16 Materials: Synthesis, Diffusion, and Sorption Properties" Dissertation, Laval University, Ste-Foy, Quebec, Canada, January 2006, in particular section 2.2; and U.S. patent application Ser. No. 15/478,794—both incorporated herein by reference in their entireties].

In a preferred embodiment, the porous silica has a surface area in the range 300 $m^2/g$ to 1400 $m^2/g$, more preferably in the range 400 $m^2/g$ to 1200 $m^2/g$, and most preferably in the range of 600 $m^2/g$ to 1000 $m^2/g$. The preferred porous silica has at least one type of pores with a diameter in the range of 1 nm to 60 nm, preferably in the range of 1 nm to 30 nm, more preferably in the range 2 nm to 10 nm, and most preferably in the range of 3 nm to 7 nm. Also, the preferred porous silica has a pore volume in the range of 0.11 cc/g to 1.5 cc/g, preferably in the range of 0.15 cc/g to 1.25 cc/g, more preferably in the range of 0.25 cc/g to 1 cc/g, and most preferably in the range of 0.5 cc/g to 0.75 cc/g.

In a preferred embodiment, the porous silica is SBA-16 which is a porous silica with large cage-like mesopores having an average pore size in the range of 1-15 nm arranged in a three dimensional cubic body-centered Im3m symmetry [Alexandridis et al. "Poly(ethylene oxide)-poly(propylene oxide)-poly(ethylene oxide) block copolymer surfactants in aqueous solutions and at interfaces: thermodynamics, structure, dynamics, and modeling" Colloids and Surfaces A: Physicochem. Eng. Aspects, 96:1-46 (1995); and Sakamoto et al. "Direct imaging of the pores and cages of three-dimensional mesoporous materials" Nature, 408(6811):449-453, 2000—each incorporated herein by reference in its entirety]. SBA-16 is synthesized under acidic conditions using a non-ionic Pluronic surfactant and has an intrawall complementary porosity. The mesophase can be created using mixtures of Pluronic P123 and Pluronic F127, or Pluronic F127 in a mixture of, for example, water and an alcohol (e.g., butanol).

Pluronic™ 123 and 127 belong to a family of polymers known as poloxamers which are nonionic triblock copolymers composed of a central hydrophobic chain of polyoxypropylene (poly(propylene oxide)) flanked by two hydrophilic chains of polyoxyethylene (poly(ethylene oxide)). Since the lengths of the polymer blocks can be customized, many different poloxamers exist that have slightly different properties. For the generic term poloxamer, these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g. P407=poloxamer with a polyoxypropylene molecular mass of 4000 g/mol and a 70% polyoxyethylene content). For Pluronic tradenames, coding of these copolymers starts with a letter to define its physical form at room temperature (L=liquid, P=paste, F=flake (solid)) followed by two or three digits, The first digit or two digits in a three-digit number in the numerical designation, multiplied by 300, indicates the approximate molecular weight of the hydrophobe; and the last digit×10 gives the percentage polyoxyethylene content (e.g., L61 indicates a polyoxypropylene molecular mass of 1800 g/mol and a 10% polyoxyethylene content). In the example given, poloxamer 181 (P181)=Pluronic L61.

The long chain polymer of Pluronic F127 produces thick pore walls. The structure of SBA-16 can be described by a triply periodic minimal surface of I-WP (body centered, wrapped package) (Sakamoto et al. 2000). Also, the mesophase may be a triply periodic minimal surface. Electron crystallography studies indicate that each mesopore is connected to eight neighboring mesopores for SBA-16 (Sakamoto et al. 2000). The pore entrance size from one mesopore to another is usually significantly smaller than the primary mesopore size. This difference in intraparticle pore sizes presents a limiting factor for applications involving intraparticle mass transfer. Desorption out of the structure is dominated by pore blocking and networking effects [Ravikovitch et al. "Density functional theory of adsorption in spherical cavities and pore size characterization of templated nanoporous silicas with cubic and three-dimensional hexagonal structures" Langmuir, 18(5):1550-1560 (2002); and Ravikovitch et al. "Experimental confirmation of different mechanisms of evaporation from ink-bottle type pores: Equilibrium, pore blocking, and cavitation" Langmuir, 18(25): 9830-9837, 2002—each incorporated herein by reference in its entirety]. The primary mesopore size can measured by diffraction or physisorption measurements in combination with an adapted geometric model like the model of spherical cavities or the triply periodic I-WP surface. In contrast, the pore entrance size is more difficult to obtain.

In other preferred embodiments, the porous silica is a silicalite, which is a polymorph of silica having a structure analogous to zeolite. The hierarchical silicalite structure includes mesopores of a hexagonal structure, and micropores. U.S. patent application Ser. No. 15/478,794 which published as US 2018/0280303—incorporated herein by reference in its entirety, discloses the synthesis of the silicalite having a particle size in the range of 1-5 nm using Ludox AS-40 and tetrapropylammonium bromide (TPABr) as silica and templating agent, respectively. The silicalite has a mesopore volume in the range of 0.11 cc/g to 1.5 cc/g, preferably in the range of 0.15 cc/g to 1.25 cc/g, more preferably in the range of 0.25 cc/g to 1 cc/g, and most preferably in the range of 0.5 cc/g to 0.75 cc/g. The silicalite has a micropore volume in the range of 0.05 cc/g to 0.1 cc/g, preferably in the range of 0.06 cc/g to 0.09 cc/g, and more preferably in the range of 0.07 cc/g to 0.08 cc/g. The hierarchical silicalite nanocarrier exhibits a hexagonal mesoporous form and silicalite form. The mesopores and micropores for the nanocarrier characterize the hierarchical structure of the mesosilicalite, wherein the mesopores form the mesophase and the micropores form the microphase. The relative weight ratios of these two phases approximate the relative weight ratios of the SiMCM-41 and silicalite used in the synthesis. The micropore diameter is in the range of about 2.0 to 2.8 nm, preferably in the range of about 2.2 to 2.6 nm, more preferably in the range of about 2.3 to 2.4. The mesopore diameter is in the range of about 2.9 to 4.0 nm, preferably in the range of 3.2 to 3.9 nm, more preferably in the range of about 3.5 to 3.8 nm, and most preferably in the range of about 3.8 to 3.9 nm. The hierarchy of the mesophase and microphase results in improved interaction with materials that can be carried, adsorbed, absorbed and/or otherwise contacted by the nanocarrier due to a greater surface area of contact with two phases instead of one phase, and an improved flow, or exchange, of the materials that may be carried into and out of the nanocarrier.

SPIONs are preferably iron oxide nanoparticles with diameter in the range of 1 to 100 nm, preferably in the range of 2 to 50 nm, more preferably in the range of 3 to 20 nm, and most preferably in the range of 5 to 15 nm. They are well-known in the art and can be obtained by various methods, see for example U.S. Pat. Nos. 9,161,996 and 8,962,031—both incorporated herein by reference in their entirety, and Szpak et al. ["Stable aqueous dispersion of supermagnetic iron oxide nanoparticles protected by charged chitosan derivatives" J. Nanopart. Res (2013) 15(1), 1372—incorporated herein by reference in its entirety]. The SPIONs are loaded on the porous silica in an amount in the range of 1 wt. % to 20 wt. %, preferably in the range 3 wt. % to 18 wt. %, more preferably in the range of 5 wt. % to 15 wt. %, and most preferably in the range of 8 wt. % to 12 wt. % of the total weight the SPIONs-porous silica. In a particularly preferred embodiment, SPIONs are loaded on the porous silica in an amount of about 10 wt. % of the total weight the SPIONs-porous silica.

Nickel oxide (NiO) nanoparticles significantly enhance the magnetization of SPIONs when co-impregnated into the silica with SPIONS. The amount of NiO co-impregnated may vary depending on the time of silica and degree of magnetization required in a specific application. In some preferred embodiments, the amount of NiO is in the range of 3 wt. % to 18 wt. %, more preferably in the range of 5 wt. % to 15 wt. %, and most preferably in the range of 8 wt. % to 12 wt. % of the total weight the SPIONs and NiO-porous silica. In a particularly preferred embodiment, NiO nanoparticles are loaded on the porous silica in an amount of about 10 wt. % of the total weight the SPIONs and NiO-porous silica.

In some preferred embodiments, the porous silica loaded with SPIONs or a mixture of SPIONs and NiO nanoparticles, is functionalized with one or more alkyltrialkoxysilane compounds. Any suitable alkytrialkoxysilane compound may be used in the functionalization reaction. The alkyltrialkoxysilane compound is preferably covalently bonded to the porous silica through an Si—R—O— bond. In a preferred embodiment, the alkyltrialkoxysilane compound is preferably selected from the group consisting of (3-aminopropyl)triethoxysilane (APTES), 3-chloropropyl trimethoxysilane, N-[-3-(trimethoxysilyl)propyl]aniline, and triethylenetetramine.

In other preferred embodiments, the functionalized porous silica loaded with SPIONs particles or a mixture of SPIONs and NiO nanoparticles, are wrapped by a biocompatible polymer. As used herein, the phrase polymer wrapping means reacting SPIONs loaded silica functionalized with aminopropyl silane with a polymer such as, but not limited to polyacrylic acid (PAA). In the case of PAA, the silane amino group reacts with the carboxyl group of PAA leading to the formation of amide bond. Biocompatible polymers are well-known in the art including, but not limited to, agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly(lactic/glycolic acid), cellulose, a cellulose derivative, a glycol, polylactide-polyglycolide, polymethyldisiloxane, polycaprolactone, polylactic acid, and ethylene vinyl acetate. In more preferred embodiments, the biocompatible polymer is selected from the group consisting of polyacrylic acid (PAA), chitosan, poly (D,L-lactide-co-glycolide), and polyethylene glycol.

The multi-functional drug composition capable of pH responsive drug release may be loaded with one or more therapeutic agents for delivery to a target diseased tissue, tumor and/or site. In some embodiments, the smart drug delivery system is loaded with one or more anticancer agents such as a mitotic inhibitor; an alkylating agent; an antimetabolite; a cell cycle inhibitor; an enzyme inhibitor; in particular, a topoisomerase inhibitor; a biological response modifier; an anti-hormone; an antiangiogenic agent such as MMP-2, MMP-9 and COX-2 inhibitor; an anti-androgen; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

In preferred embodiments of the invention, the multi-functional drug composition capable of pH responsive drug release is loaded with a platinum(II) complex effective for the treatment of cancer. Many platinum(II) complexes effective for treatment of cancer are well-known in the art including. Any platinum(II) complexes effective for treatment of cancer can be used as the drug treatment agent of the smart drug delivery system including, but not limited to, cisplatin, carboplatin, oxaliplatin, nedaplatin, triplatin tetranitrate, phenanthriplatin, picoplatin, strataplatin or mixtures thereof. In a preferred embodiment, the platinum(II) complex is at least one of cisplatin, carboplatin, oxaliplatin, and nedaplatin. The one or more platinum(II) complexes may be loaded on the smart delivery system in amount in the range of 0.001 to 1.80 mmol/g, preferably in the range of 0.01 to 1.2 mmol/g, more preferably 0.1 to 1.0 mmol/g, and most preferably 0.9 mmol/g of the total weight of the smart drug delivery system.

A second aspect of the invention is directed to a method of making the multi-functional drug composition capable of pH responsive drug release of the invention. The method includes:

impregnating a porous silica nanocarrier with SPIONs or a mixture of SPIONs and NiO nanoparticles, functionalizing the SPIONs impregnated porous silica nanocarrier with a silane compound, reacting the functionalized SPIONs impregnated porous silica nanocarrier with a polymer, for example by heating a mixture of biocompatible polymer and the nanocarrier at a temperature in the range of 120° C. to 180° C. in a solvent for a sufficient time (e.g., in the range of 0.5 hour to 5.0 hours), to form a polymer-containing composition mixing the polymer-containing composition and a drug or pharmaceutical agent to form a mixture, optionally stirring the mixture for about 16 to 40 hours, and optionally separating the nanocarrier loaded with the drug.

Any silane compound suitable to functionalize the porous silica may be used. In a preferred embodiment the silane compound is selected from the group consisting of (3-aminopropyl)triethoxysilane (APTES), 3-chloropropyl trimethoxysilane, N-[-3-(trimethoxysilyl)propyl]aniline, and triethylenetetramine. In a particularly, preferred embodiment, the silane is (3-aminopropyl)triethoxysilane (APTES).

The solvent is preferably an organic solvent suitable for encapsulated the functionalized SPIONs or a mixture of SPIONs and NiO nanoparticles. In a preferred embodiment, the organic solvent is an aprotic polar solvent, such as, but not limited to, dimethyl formamide, dimethyl sulfoxide, acetonitrile, acetone, tetrahydrofuran, and dioxane. In a particularly preferred embodiment, the organic solvent is dimethyl formamide.

The mixture is preferably heated in the solvent, optionally under an inert gas such as argon or nitrogen, to a temperature in the range 100° C. to 180° C., preferably in the range of 110° C. to 165° C., more preferably in the range of 120° C. to 155° C., and most preferably in the range 135° C. to 145° C. In a preferred embodiment, the mixture is heated at about 140° C. for about two hours.

In other embodiments the mixture is heated in the solvent for a time in the range of 0.5 hour to about 5.0 hours, preferably in the range of 1 hour to 4.0 hours, more preferably in the range of 1.5 hour to 3.0 hours, most preferably for about 2 hours.

The drug may be loaded on the encapsulated functionalized SPIONs impregnated porous silica nanocarrier wrapped with biocompatible polymer by stirring a solution (preferably a saline solution) of the drug with the carrier, preferably in the dark, preferably at a reduced temperature, e.g., about 4° C. for a time in the range of 1 hour to 12 hours, preferably 2 hours to 10 hours, more preferably 3 hours to 8 hours, and most preferably about four hours.

Pharmaceutical Composition:

A Third aspect of the invention is directed to a pharmaceutical composition comprising the multi-functional drug composition capable of pH responsive drug release of the invention. Any drug that needs to be targeted to a particular diseased tissue may be loaded on the smart delivery system of the invention.

In preferred embodiments, the pharmaceutical composition comprises the multi-functional drug composition capable of pH responsive drug release of the invention loaded with a platinum(II) complex effective for the treatment of cancer in an amount in the range of 0.001 to 1.80 mmol/g of the total weight of the smart drug, more preferably in the range of 0.0025 to 1.50 mmol/g of the total weight of the smart drug, even more preferably in the range of 0.05 to 1.20 mmol/g of the total weight of smart drug, and most preferably 0.01 to 0.9 mmol/g of the total weight of the multi-functional drug composition.

In a particularly preferred embodiment, the pharmaceutical composition comprises the multi-functional drug composition capable of pH responsive drug release of the invention loaded with about 0.011 mmol or 0.9 mmol of the platinum(II) complex per gram of the total weight of the composition.

In another preferred embodiment, the pharmaceutical composition comprises the multi-functional drug composition of the invention loaded with one or more platinum(II) complexes such as, but not limited to, cisplatin, carboplatin, oxaliplatin, nedaplatin, triplatin tetranitrate, phenanthriplatin, picoplatin, or stratoplatin. In a more preferred embodiment, the loaded platinum(II) complex is selected from the group consisting of cisplatin, carboplatin, oxaliplatin, and nedaplatin. In the most preferred embodiment, the loaded platinum(II) complex is cisplatin.

In one or more embodiments, the pharmaceutical composition comprises at least 0.1 wt. %, 0.5 wt. %, 5 wt. %, 10 wt. %, 15 wt. %, 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, 95 wt. %, 99 wt. %, or 99.9 wt. % of the multi-functional drug composition of the invention loaded with the platinum(II) complex relative to the total weight of the pharmaceutical composition. Preferably, the pharmaceutical composition may further comprise one or more pharmaceutically acceptable binders, such as sucrose, lactose, glucose, fructose, galactose, mannitol, xylitol, and/or pharmaceutically acceptable excipients such as calcium carbonate and calcium phosphate.

In some embodiments, the ability of the active ingredient to reduce the viability of cancer cells may be determined by contacting the pharmaceutical composition with the cancer cells and then performing cell viability assays. Methods of such assays include, without limitation, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, colon cancer cell lines, e.g., HCT15, MDST8, GPSd, HCT116, DLD1, HT29, SW620, SW403 and T84, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA-1, HRS, and C-41, ovarian cancer cell lines, e.g., A2780, A2780cis, OV7, and PEO23, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably colon cancer, lung cancer, cervical cancer, testicular cancer, and/or breast cancer. In at least one embodiment, cisplatin-resistant cancer cells are used. These cells may be generated by culturing cancer cells with low doses of cisplatin in order to build their resistance to cisplatin while maintaining cell viability. Examples of cisplatin-resistant cancer cells include, but are not limited to, A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

In a preferred embodiment, the pharmaceutical composition comprises 0.1-400 µM of the platinum(II) complex or anticancer agent relative to the total volume of the composition.

In another preferred embodiment, the pharmaceutical composition comprises one or more carriers and/or excipients selected from the group consisting of a buffer, an inorganic salt, a fatty acid, a vegetable oil, a synthetic fatty ester, a surfactant, a sugar, a polymer, and combination thereof.

In another preferred embodiment, the pharmaceutical composition may comprise other active ingredients in addition to the multi-functional drug composition capable of pH responsive drug release containing the platinum(II) complex. In one embodiment, one or more other active ingredients may be a chemotherapeutic agent or an anticancer agent, for the treatment or prevention of neoplasm, tumor or cancer cell division, growth, proliferation and/or metastasis in the subject; induction of death or apoptosis of tumor and/or cancer cells; and/or any other forms of proliferative disorder.

The anticancer agent is preferably at least one of a mitotic inhibitor; an alkylating agent; an antimetabolite; a cell cycle inhibitor; an enzyme; a topoisomerase inhibitor; a biological response modifier; an anti-hormone; an antiangiogenic agent such as MMP-2, MMP-9 and COX-2 inhibitor; an anti-androgen; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well-known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, poly alkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition having the smart drug delivery system responsive to pH loaded with a platinum(II) complex disclosed herein thereof has different release rates categorized as immediate release and controlled- or sustained-release.

A fourth aspect of the invention is related to a method for treating a proliferative tissues in a patient, comprising administering to a subject in need of therapy an effective amount of a pharmaceutical composition comprising the multi-functional drug composition capable of pH responsive drug release containing the platinum(II) complex, wherein the proliferative disorder is cancer and/or tumor.

The presence of the SPIONs in the smart delivery system serves two purposes. The first is to aid targeting the drug to a particular diseased tissue by applying external magnetic field to the diseased tissues, and thereby concentrating the drug in the diseased tissues in need of treatment and minimize the drug contacts with healthy tissues. The second is that SPIONs are magnetic contrasting agent used in magnetic resonance (MRI) imaging. Thus, the method of treatment may involve a combination of administering effective amount of the drug to a subject, while observing and targeting the drug to the diseased tissue by an applied external magnetic field.

As used herein, the terms "treat", "treatment", and "treating" in the context of the administration of a therapy to a subject in need thereof refers to the reduction or inhibition of the progression and/or duration of a disease (e.g. cancer), the reduction or amelioration of the severity of the disease, and/or the amelioration of one or more symptoms thereof resulting from the administration of one or more therapies.

"Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumour size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the proliferative disorder is cancer. In some embodiments, the disclosed method of the fourth aspect is for treating cancer of the blood, brain, bladder, lung, cervix, ovary, colon, rectum, pancreas, skin, prostate gland, stomach, breast, spleen, liver, kidney, head, neck, testicle, bone, bone marrow, thyroid gland, or central nervous system. In a preferred embodiment, the cancer is at least one selected from the group consisting of colon cancer, cervical cancer, breast cancer, and lung cancer. In a more preferred embodiment, the cancer is cervical cancer or breast cancer. In the most preferred embodiment, the cancer is cervical cancer or breast cancer.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e. g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In one or more embodiments, the pharmaceutical composition administered comprises the smart drug delivery system responsive to pH drug release loaded with one or more platinum(II) complex.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or "sufficient amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount is in the range of 0.1-30 g/kg of the smart drug delivery system responsive to pH drug release loaded with on woe more the platinum(II) complex per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering a pharmaceutical composition containing the multi-functional drug composition capable of pH responsive drug release loaded with one or more platinum(II) complex of the current disclosure as a single dose or multiple individual divided doses and applying a magnetic field to the diseased tissue, wherein the smart drug is accumulated and releases the loaded platinum(II) complex in or nearby the diseased tissues. In some embodiments, the composition is administered at various dosages (e.g. a first dose with an effective amount of smart drug delivery system responsive to pH drug release comprising 200 mg of the platinum(II) complex per kilogram of the subject and a second dose with an effective amount of the smart drug comprising 50 mg of the platinum (II) complex per kilogram of the subject). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments of treatment, the method further comprises measuring a concentration of a biomarker and/or detecting a mutation in a biomarker before and/or after the pharmaceutical composition comprising the multi-functional drug composition capable of pH responsive drug release with the platinum(II) complex of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Exemplary biomarkers for lung cancer include, without limitation, CA 125, CA 15-3, EGF receptor, anaplastic lymphoma kinase gene, MET, ROS-1, and KRAS. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the smart drug delivery system responsive to pH drug release loaded with the platinum(II) complex by at least 5%, at least 10%, or at least 30%, up to 50%, up to 60%, or up to 80% of an initial effective amount nanocarrier loaded with platinum(II) complex that contains in the range of 1-300 mg of the platinum(II) complex per kilogram of the body weight of the subject. The increased effective amount may be in a range of 1.05-540 mg/kg, preferably 15-420 mg/kg, more preferably 25-270 mg/kg. The subject may be administered with the increased dosage for a longer period (e.g. one more week, 2 more weeks, or 2 more months) than the duration prescribed with the initial effective amount.

In some embodiments, the mutation in the biomarker is detected before administering the composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Example 1

Methods and Materials:

Characterization: The X-ray diffraction patterns for mesostructured silicas were obtained on a bench top Rigaku Multiplex system. The textural characteristics including surface area, pore volume and pore size distribution were measured on an ASAP-2020 plus, and accelerated surface area and porosity were determined on Micromeritics, Norcross, Ga., USA. The cisplatin functional groups were identified using Fourier transform infrared spectroscopy (Perkin Elmer) equipped with attenuated total reflectance (ATR). Surface morphologies were measured using transmission electron microscope (TEM, FEI, Morgagni, Czec Republic). TEM samples were prepared by dropping particle dispersions onto carbon-coated Cu grids and air-dried before mounting on a microscope. Particle sizes were determined from electronic images using Gatan digital micrograph software. The data is presented in the form of average number for each specimen with standard deviation.

Material

Four types of nanocarriers were used: SBA-16, mesosilicalite, monodisperse spherical silica (purchased commercially from Superior Silica, USA and superhydrophobic spherical silica. SBA-16 was prepared by the hydrothermal method using the triblock copolymer Pluronic F127 as a template. Similarly, mesosilicalite was prepared as previously described in U.S. patent application Ser. Nos. 15/478,794 and 15/992,953—incorporated herein by reference in their entireties by the hydrothermal method using cetyl trimethyl ammonium bromide as a template.

Drug Release:

For the drug release study, cellulose membrane (MWCO=14,000) dialysis tubing was used to study the drug release at pH 5.0 and 7.0. The dialysis bags were treated with 100 ml PBS solution for 30 min. Drug delivery system (30 mg) was mixed with 3 ml of PBS, pH 5.0 or pH 7.0, in the treated dialysis bag. Then, the dialysis bag was inserted in 100 ml beaker containing 47 ml of PBS at 37° C. and the amount of drug released from the bag was determined. At specific period, 10 ml of the solution was withdrawn and replaced with equal volume of fresh PBS solution. Then, the release amount was calculated based on the calibration curve at a specified wavelength of 208 nm.

Example 2

SPIONs/mesopore silica was then functionalized with different types of silanes such as 3-aminopropyl)triethoxysilane (APTES), 3-chloropropyl trimethoxysilane, N-[-3-(trimethoxysilyl)propyl]aniline silane, and triethylenetetramine. Before functionalization, the silica was predried at 120° C. overnight. Then 2.2 g of support was added in anhydrous toluene (220 ml) under argon atmosphere and stirred for 10 min. Silane (3.3 ml) was added and refluxed at 110° C. for 2 h. The resulting mixture was filtered and vacuum dried for 2 h.

For pH responsive drug release, the SPIONs/meso silica composite was fabricated by heating the composite in a solution of polyacrylic acid (PAA) in dimethyl formamide under reflux (140° C. for 2 h) in Argon atmosphere at Schenk line apparatus. The SPIONs/Silica/APTES/PAA composite was then filtered using glass funnel with filter using vacuum pump, washed with methanol (5 ml) thrice and then kept for drying at ambient condition.

Example 3

Figure 7:
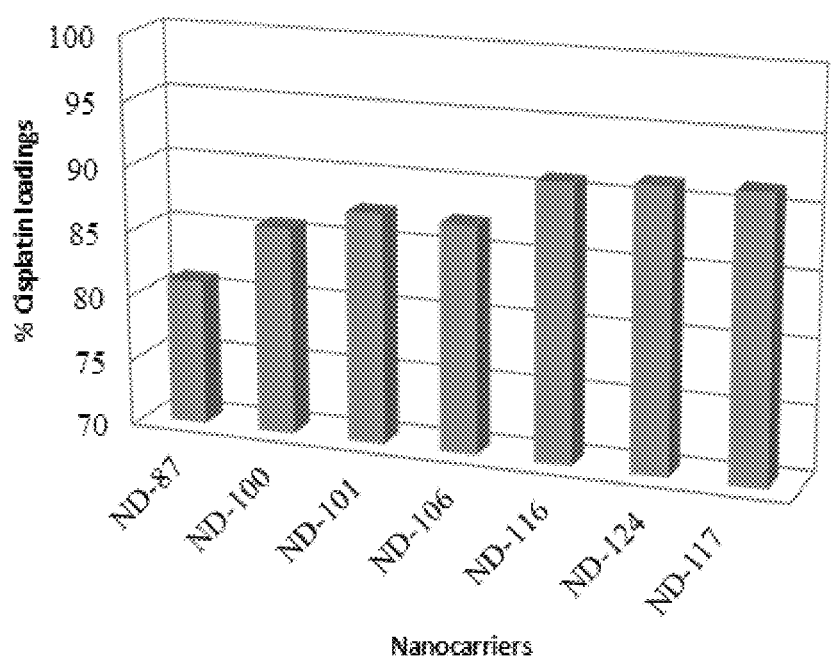
FIG. 7 shows the adsorption capacity over different types of nanoformulations in normal saline for 24 h.

The meso type silica S-16 was impregnated with diagnostic property induced metal oxides specifically superparamagnetic iron oxide nanoparticles (termed as SPIONs) through enforced adsorption technique. In a typical preparation, a 10 ml saline solution containing cisplatin (30 mg) was mixed with SPIONs/silica(APTMS)/silane/PAA composite (600 mg) and the mixture was stirred in an ice cooled dark environment. The cisplatin composite was filtered, washed and dried at room temperature. The sample was then stored at 4° C. The filtrate and washing saline were collected and the amount cisplatin in solution was estimated using the UV absorption at 208 nm and Beer-Lambert's law. The loading on the nanocarrier was estimated by subtracting the amount of cisplatin in solution from that of the total amount contained in the saline solution. The same method was used to prepare and calculate the loading of all cisplatin/SPIONs/silica preparations. FIG. 7 shows the adsorption capacity over different types of nanoformulations ND87 (Site/M41), ND-100 (APTES/MSU-Foam), ND-101 (F127/SiSBA-16), ND-106 (SiSBA-16), ND-116 (E/10 wt % SPIONs/S-16), ND-124 (APTES/spherical silica), and ND-117 (SPIONs/S-16/APTES/PAA) in normal saline for 24 h. The result shows that three nanoformulations ND-116, ND-124 and ND-117 exhibited highest drug adsorption capacity (~91%) than other nanoformulations. The physical mixture of silicalite and SiMCM-41 (ND-87) showed the lowest cisplatin adsorption of 81%.

Example 4

Figure 1B:
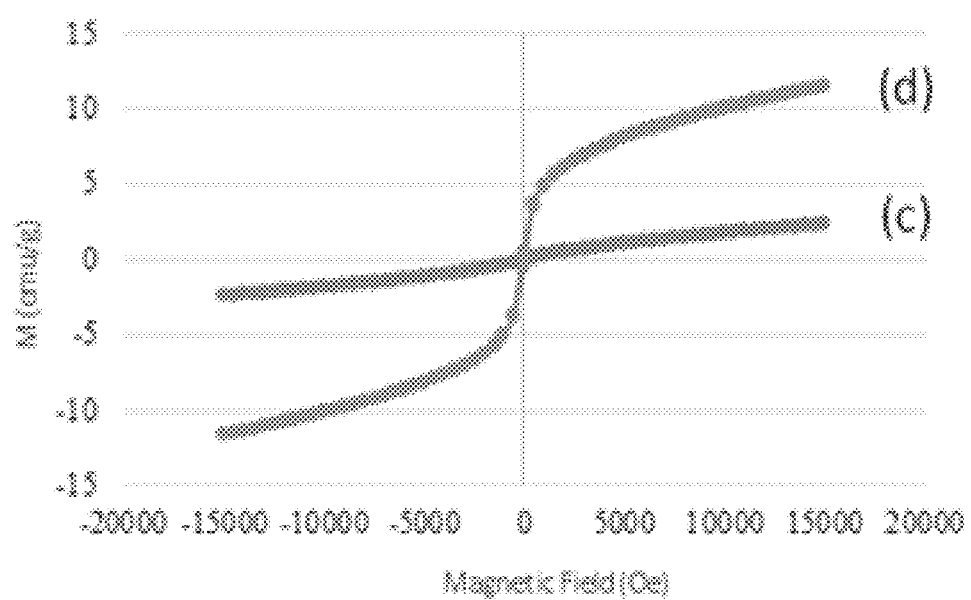
FIG. 1B shows VSM analysis (c) 10wtFe/S-16 (ND-95) and (d) 10wtFe10wtNi/S-16 (ND-91).
Figure 1C:
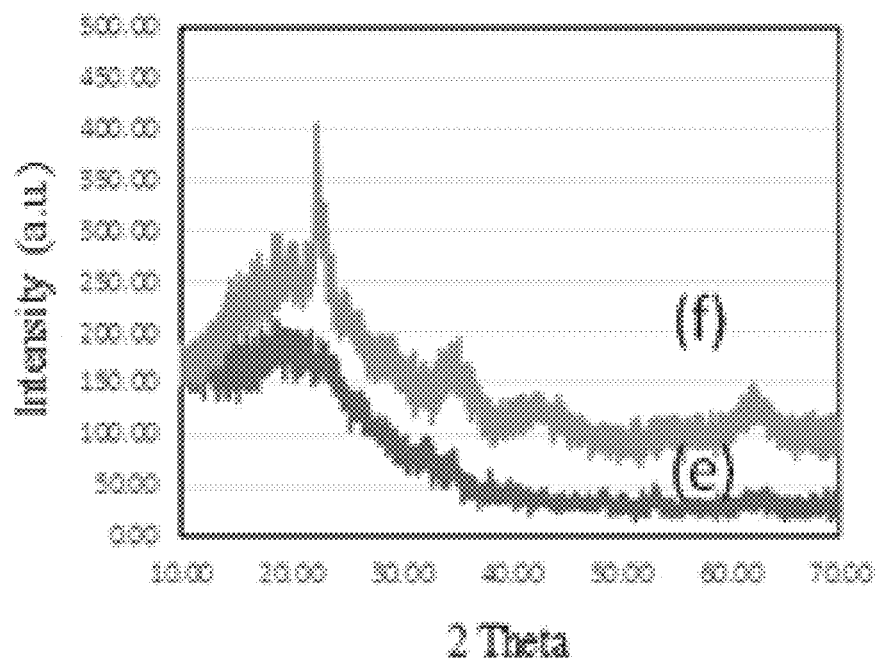
FIG. 1C shows XRD diffraction patterns (e) 10wtFe/mesosilicalite (ND-43) and (f) 10wtFe10wtNi/mesosilicalite (ND-90).
Figure 1D:
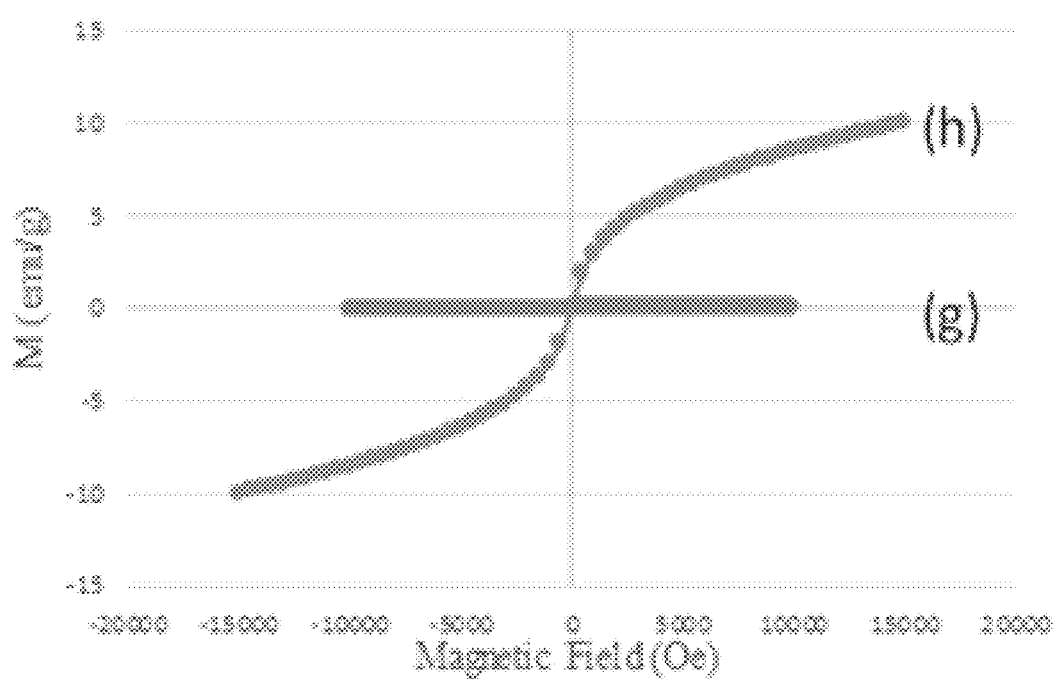
FIG. 1D shows VSM analysis (g) 10wtFe/mesosilicalite (ND-43) and (h) 10wtFe10wtNi/mesosilicalite (ND-90).
Figure 2:
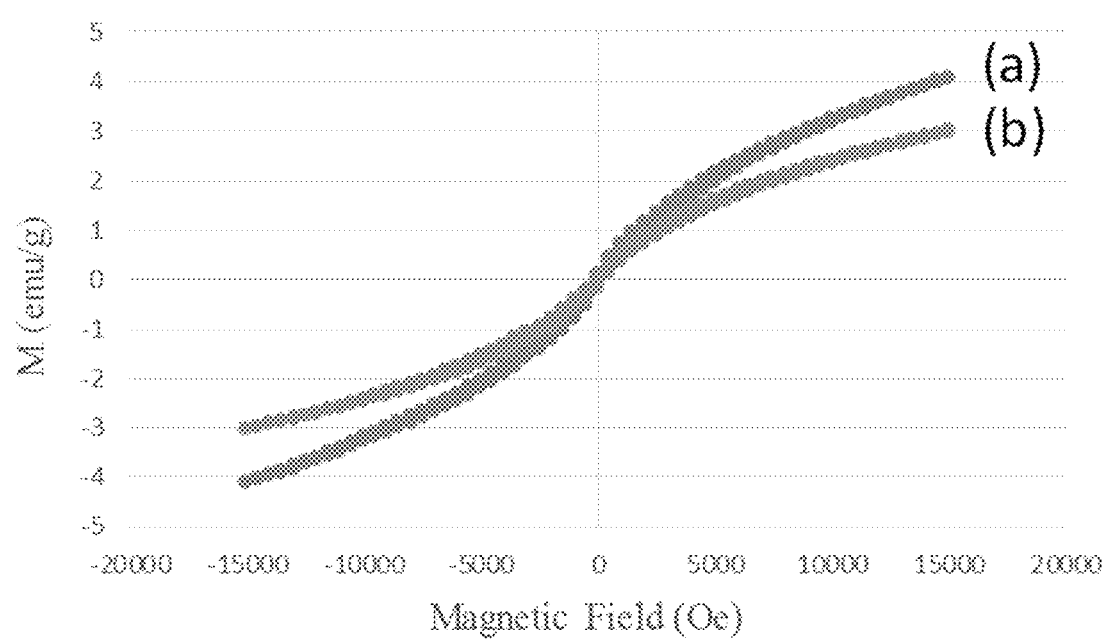
FIG. 2 shows the VSM analysis of (a) 10wtFe/ND-88 and (b) 10wtFe/ND-89.

Influence of Mono and Bimetal Oxide Loadings
(a) X-Ray Diffraction (XRD) Analysis:

FIGS. 1 and 2 show XRD diffractions and magnetic properties measured by vibrating sample magnetometer (VSM) of SPIONs loaded on structured silicas. Four types of nanocarriers were used: (1) S-16 (2) mesosilicalite, (3) monodisperse spherical silica and (4) superhydrophobic spherical silica. The particle sizes of S-16 and mesosilicalite were in the range 1-5 nm, whereas those of spherical silica and superhydrophobic silica were 80 nm. Different weight percentages of metal oxide loadings were carried out using enforced adsorption technique. The presence of $Fe_3O_4$ was expected to be observed at 2θ value of 35.45°. The XRD pattern of (ND-95) showed a weak peak due to small nanosize $Fe_3O_4$ particles clearly indicating lack of crystallization at the nanopores of the nanocarrier [FIG. 1A (a)]. The sample containing 10 wt. % iron oxide and 10 wt. % nickel oxide loaded on SBA-16 (ND-91) showed characteristic reflections at 2θ values equal to 35°, 43° and 61° corresponding to the presence of NiO species. The peaks at 2θ values corresponding to 9° and 20° becomes difficult to identify the diffraction patterns of NiO due to overlap between broad peaks of amorphous silica, and also the crystallite size of the dispersed NiO species on support is near detection limit of XRD [FIG. 1A (b)]. The presence of broad peaks shows the presence of nickel species in a crystalline phase nanometer size particles. The presence of broad peaks is in good correlation with the high surface area of samples that reflects finer particles dispersed on the 3D cage type of mesoporous silica (Table 2). [Nash—where is table 2?] In case of 10 wt. % iron oxide 10 wt. % nickel oxide loaded on mesosilicalite (ND-90), diffractions patterns of hexagonal mesophase and silicalite microphase similar to that of the parent mesosilicalite were observed. Similar to Si-SBA-16, the sample with 10 wt. % Ni loaded showed characteristic reflections at 2θ values equal to 35°, 43° and 61° corresponding to the presence of NiO species [FIG. 1C (e) and (f)].

(b) VSM Analysis:

The magnetic properties of designed nanoparticle composites are measured using vibrating sample magnetometer (VSM). The VSM study shows the transformation of magnetically inactive nanoformulation with respect to 3D cage type of siliceous SBA-16 and mesoporous silicalite into super paramagnetically active nano-formulations. FIG. 1B (c) and (d) shows VSM analysis of 10 wt. % iron oxide loaded on SBA-16 and 10 wt. % iron oxide 10 wt. % nickel oxide loaded on SBA-16, respectively. The addition of nickel resulted in mixed metal oxide species and generated magnetically active composite. In case of mesoporous silicalite, even the increment of iron oxide species from 10 to 15 wt. % failed to generate magnetically active composite. In contrast, addition of nickel oxide tends to favor super paramagnetic composite. 10 wt. % iron oxide loaded on S-16 and mesosilicalite generated magnetization value of 2.39 and 0.039 emu/g, respectively. Also, the result shows that the magnetization value is significantly increased by co-impregnation with additional metal oxide such as nickel oxide. FIGS. 1A (a) and 1B (c) show that 10 wt. % iron oxide tends to generate 2.39 emu/g, while co-impregnation of nickel oxide and iron oxide increases the magnetic property significantly to 11.5 emu/g [FIG. 1B (c) and (d)]. Similarly, in case of mesosilicalite nanocarrier, 10 wt % iron oxide showed 0.039 emu/g [FIG. 1C (e) and (f)], while the presence of nickel oxide generated mixed metal oxides and significantly increased magnetization to 10 emu/g [FIG. 1D (g) and (h)].

Example 5

Influence of Hydrophilic and Hydrophobic Property of Silica

The influence of hydrophilic and hydrophobic surface of spherical silica was studied for magnetization. The hydrophilic surface of silica is modified by treating with alkylchlorosilanes, trimethylsilanol in argon atmosphere, similar to the procedure of silane functionalization described in example 2. Multifunctional monodisperse spherical silica impregnated with iron oxide was prepared using enforced adsorption technique described above. The spherical silica particle size was 80 nm [FIG. 2 (a)]. The external surface of magnetically active silica nanoparticle can be modified. FIG. 2 (b) shows the magnetically modified super hydrophobic silica nanoparticle. FIG. 2 (a) shows that 10 wt. % iron oxide tends to generate 4.09 emu/g, whereas impregnation of iron oxide in highly hydrophobic spherical silica decreases the magnetic property to 3.0 emu/g [FIG. 2 (b)].

Example 6

Influence of Calcination Temperature

Figure 3:
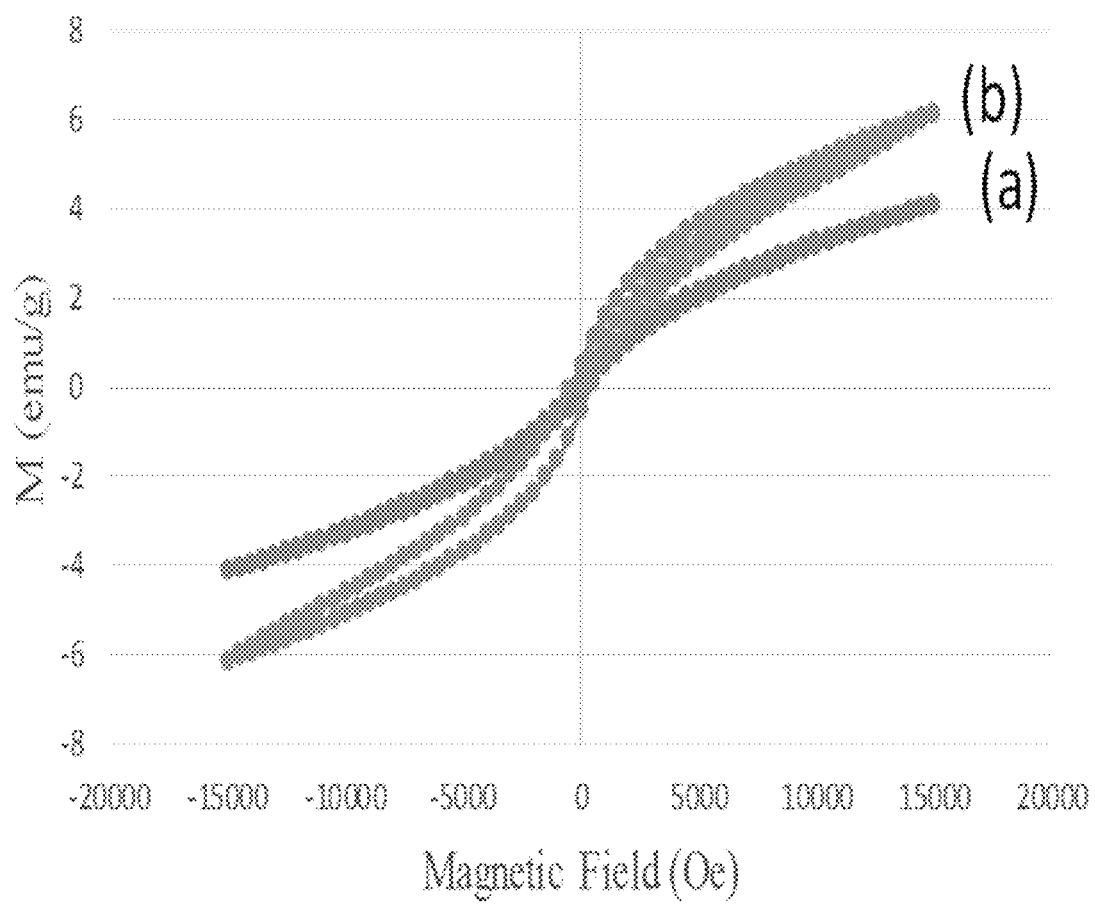
FIG. 3 shows the VSM analysis of (c) 10wtFe/ND-88 calcined at 500° C. for 2 h and (d) 10wtFe/ND-88 calcined at 750° C. for 2 h.

The influence of calcination temperature was studied at 500° C. and 750° C. over hydrophilic surface of spherical silica for magnetization effect. An increase in the magnetization was observed with increase in the calcination temperature. FIG. 3 (a) shows magnetization of 4.09 emu/g for a sample calcined at 500° C., and the magnetization of 6.13 emu/g (FIG. 3b) for a sample calcined at 750° C.

Example 7

Fabrication and Characterization of Multifunctional Drug Delivery

Figure 4:
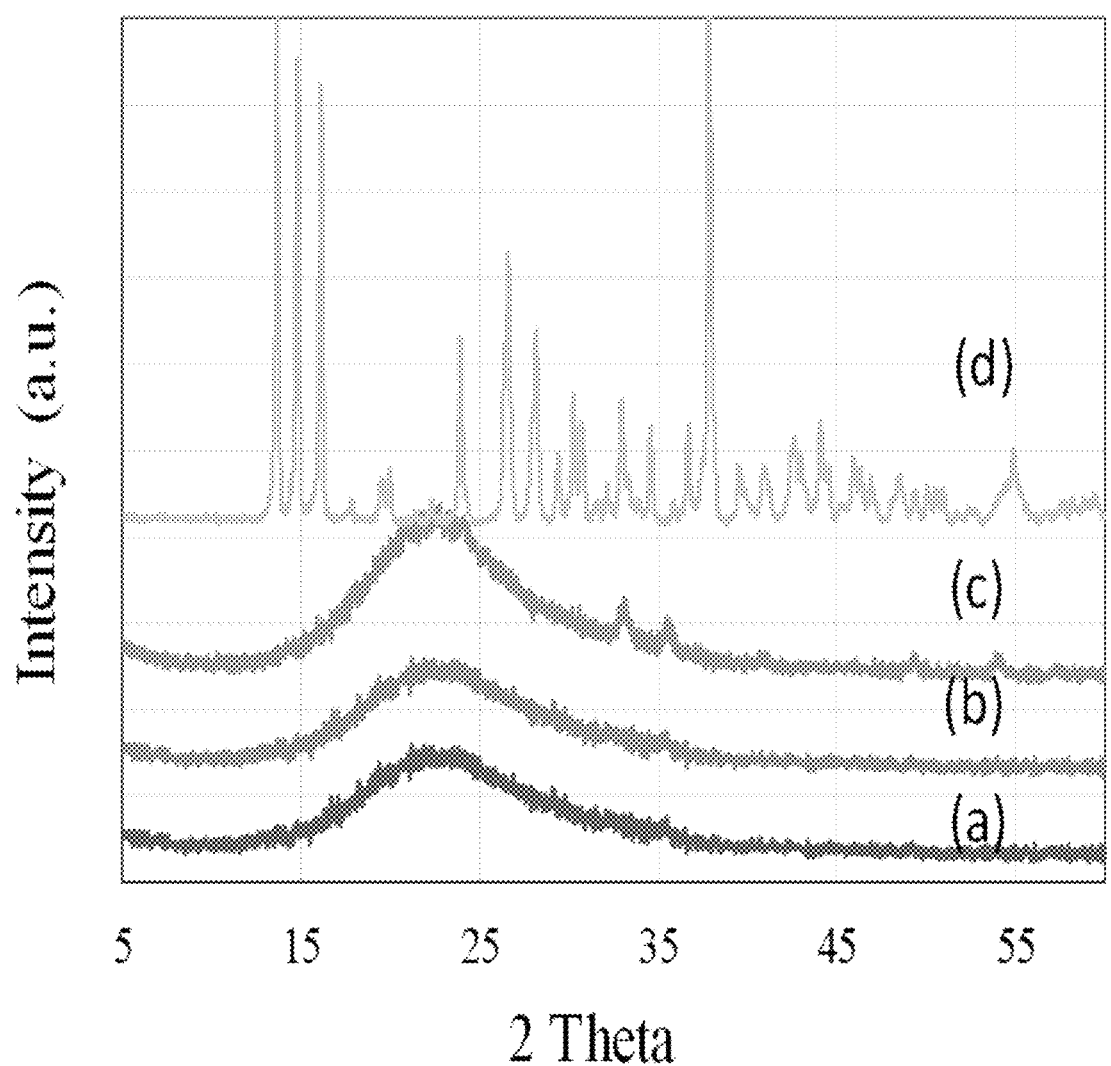
FIG. 4 X-ray diffraction pattern of (a) ND-95 (10wtFe/S-16); (b) ND108 (10wtFe/S-16-APTMS); (c) ND-117 (10wtFe/S-16-APTES-PAA-Cp) and (d) Cisplatin.
Figure 5A:
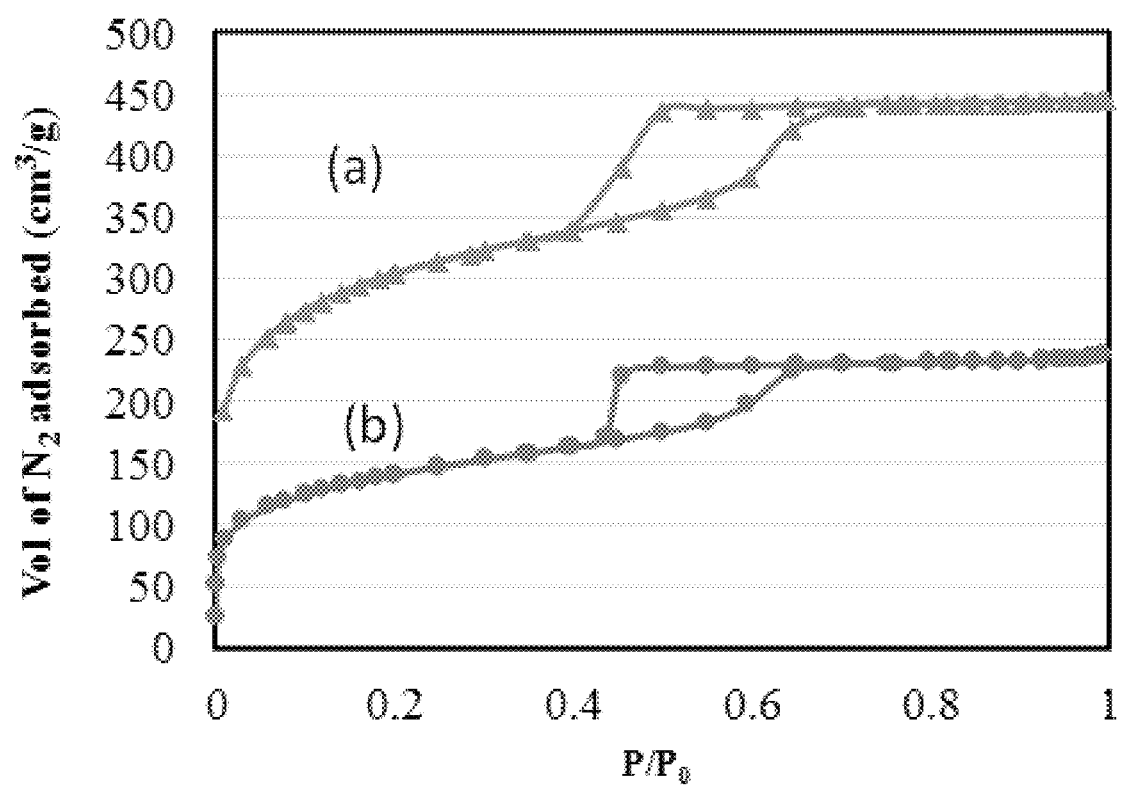
FIG. 5A shows BET surface area (a) Si-16 and (b) ND-117 (SPIONs/Si-16/APTES/PAA/cisplatin).
Figure 5B:
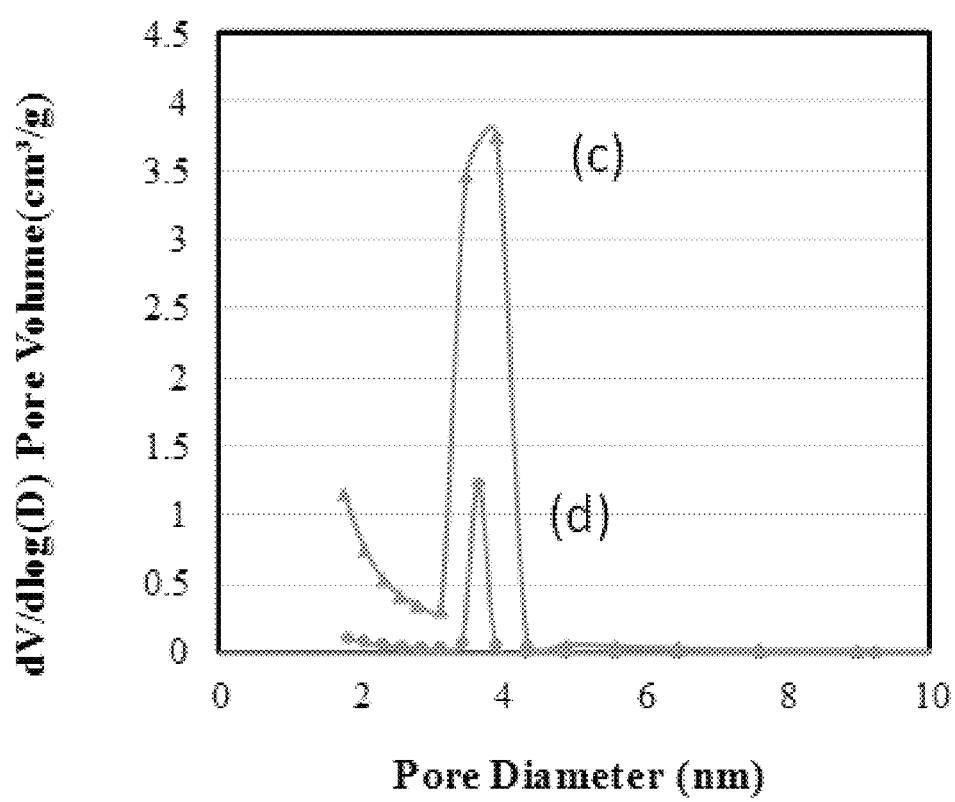
FIG. 5B shows pores size distributions of (c) Si-16 and (d) ND-117 (SPIONs/Si-16/APTES/PAA/cisplatin)
Figure 5C:
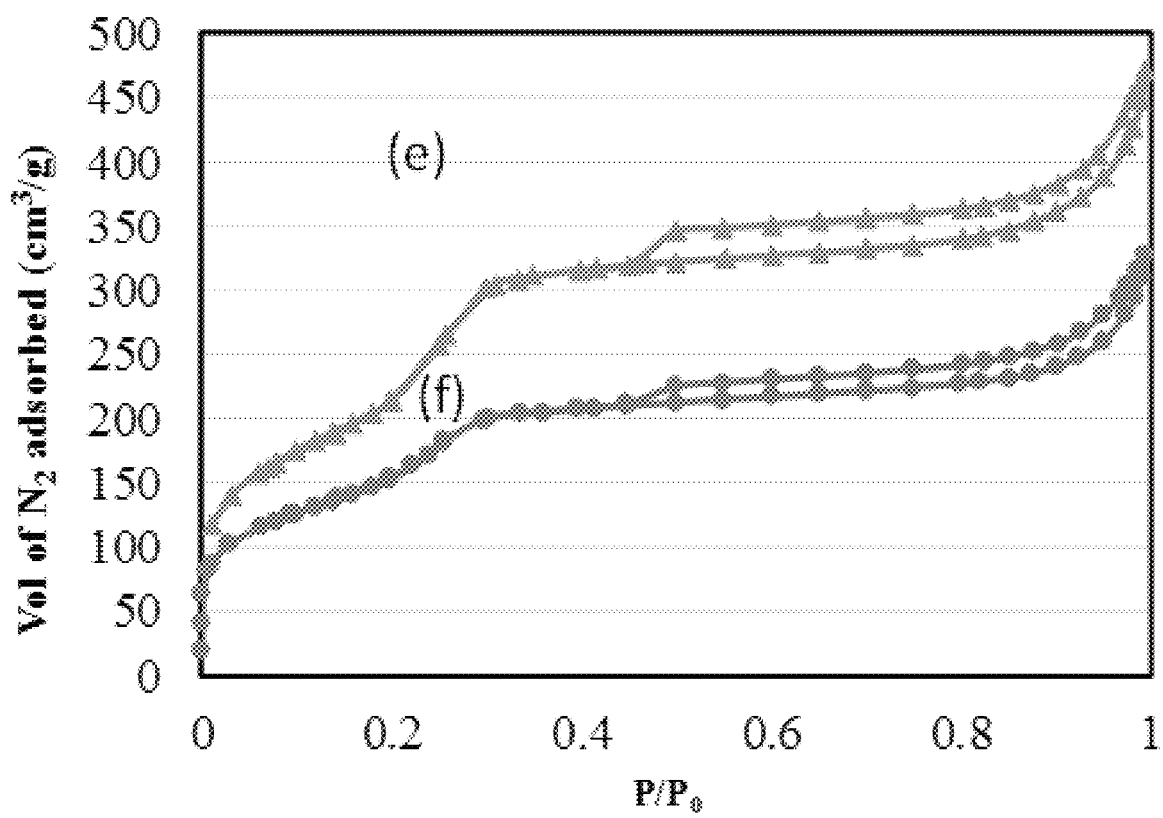
FIG. 5C shows the BET surface area of (e) mesosilicalite and (0 ND-90 (SPIONs/mesosilicalite/APTES/PAA/cisplatin.
Figure 5D:
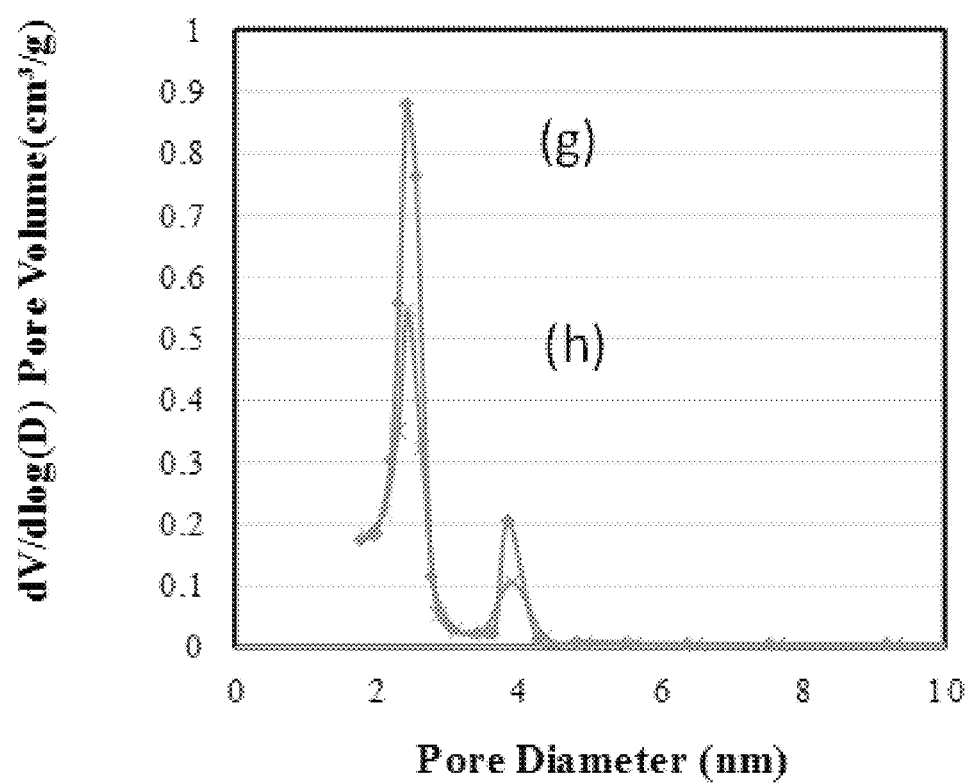
FIG. 5D shows pores size distributions of (g) mesosilicalite and (h) ND-90 (SPIONs/mesosilicalite/APTES/PAA/cisplatin.

The XRD pattern of 10 wt. % iron oxide/S-16 (ND-95), ND-95 after silylation with APTES (ND108), ND108 after wrapping with polyacrylic, acid and cisplatin (ND-117), and cisplatin alone are shown in FIG. 4 [(a)-(d), respectively]. FIG. 4 (a) shows the presence of amorphous nanosized $Fe_3O_4$ particles at nanopores of the nanocarrier. The silylation did not show much change in the diffraction pattern [FIG. 4 (b)]. In contrast, polyacrylic acid wrapped composite with cisplatin loading tends to show similar amorphous transformation of crystalline cisplatin, while some distinct peaks for cisplatin after silylation indicates the presence of weak crystalline cisplatin at the external surface of mesopores due to silane functionalization [FIG. 4 (c) and (d)].

Example 8

BET Surface Area and Pore Size Distribution

Table 1 summarizes the BET surface area and pore size distributions of Si-16, ND-117 (SPIONs/Si-16/APTES/PAA/cisplatin), mesosilicalite and ND-90 (SPIONs/mesosilicalite/APTES/PAA/cisplatin), respectively.

TABLE 1

| Sample | Composite | BET Surface area ($m^2/g$) | BJH adsorption cumulative surface area ($m^2/g$) | t-plot micropore surface area ($m^2/g$) | Pore volume ($cm^3/g$) | Pore diameter (desorption) (nm) | |
|---|---|---|---|---|---|---|---|
| SiSBA-16 | S-16 | 988 | 590 | 340 | 0.69 | 3.3 | — |
| ND-117 | S-16 | 471 | 297 | 127 | 0.37 | 3.8 | — |
| Mesosilicalite | Site/M41 | 954 | 900 | 295 | 0.73 | 2.4 | 3.8 |
| ND-90 | Site/M41 | 632 | 604 | — | 0.48 | 2.4 | 3.6 |

In the case of 3D cubic SBA-16, a significant decrease in the textural characteristics was observed. Specifically, a decrease of specific surface area from 988 $m^2/g$ to 471 $m^2/g$, and cumulative surface area from 590 $m^2/g$ to 297 $m^2/g$, which is about 50% of $Fe_2O_3$ occupation was observed after iron oxide impregnation. The cumulative pore volume showed a similar occupation (46%) compared to parent SiSBA-16.

Mesosilicalite nanocarrier showed highest surface area of 954 m2/g, pore volume of 0.73 cc/g and dual pores of 2.4 nm and 3.8 nm. SPIONs are well accommodated in the available large surface area and hierarchical pores. Surface occupation is about 33%. The micropores were effectively filled along with mesopores indicating easy pore accessibility than S-16 support. In particular, micropore surface area of S-16 reduced from 340 m²/g to 127 m²/g, while complete filling occurs over mesosilicalite, which showed complete reduction of surface area from 295 m²/g.

Example 9

FT Infra-Red Analysis

Figure 6:
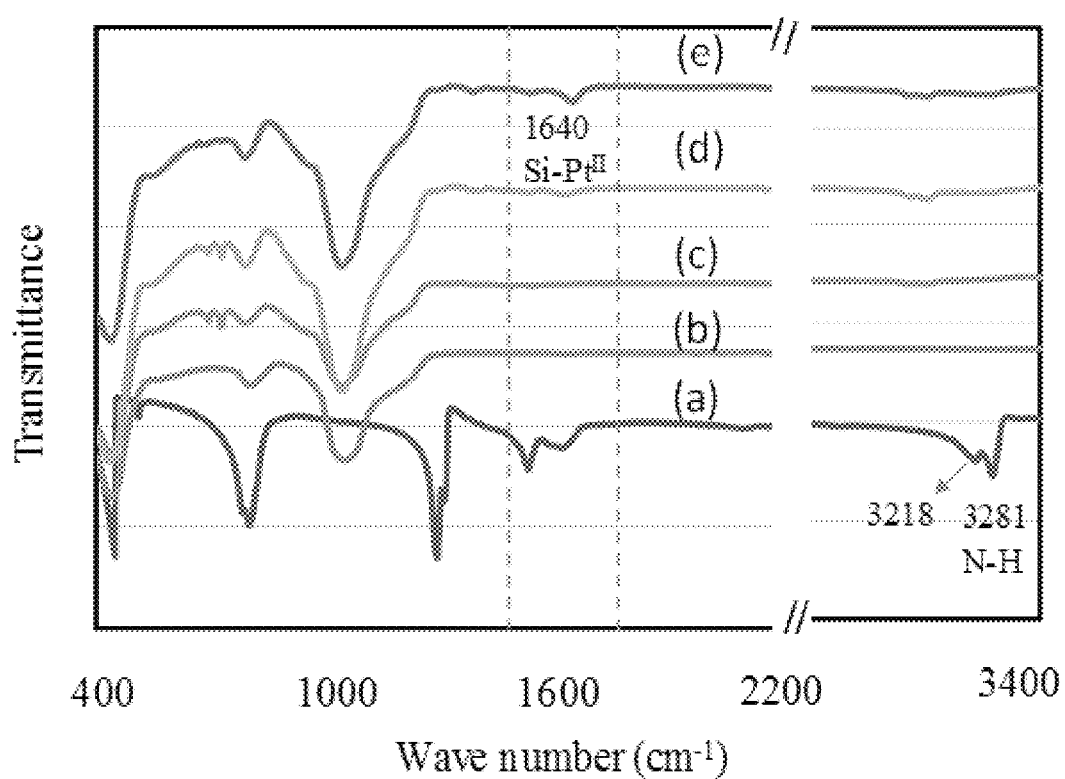
FIG. 6 shows the FTIR spectra of (a) Cisplatin (b) Si-16 (c) ND-108 (10wtFe/Si-16/APTES); (d) ND116 (10wtFe/Si-16/APTES/Cp); and (e) ND-117 (10wtFe+APTES+PAA+Cp).

Cisplatin showed an intense amine stretching band at v 3218 and 3281 cm⁻¹. A broad peak of 1640 cm⁻¹ shows the characteristic peaks of cisplatin [FIG. 6 (a)]. A characteristics FTIR profile of nanocarrier Si-16 and Si-16 after impregnation followed by silane functionalization (ND-108) were observed in FIGS. 6 (b) and 6 (c). In case of ND116 and ND117, the presence of weak amine band shows the conjugation between silane NH2 and Cl bond of cisplatin. In addition, the presence of bending vibration at 1640 cm⁻¹ indicates the functionalization of cisplatin and reaction between silica and Pt$^{II}$ complex [FIG. 6 (d) and (e)].

Example 10 pH Responsive Cisplatin Drug Release

Figure 8:
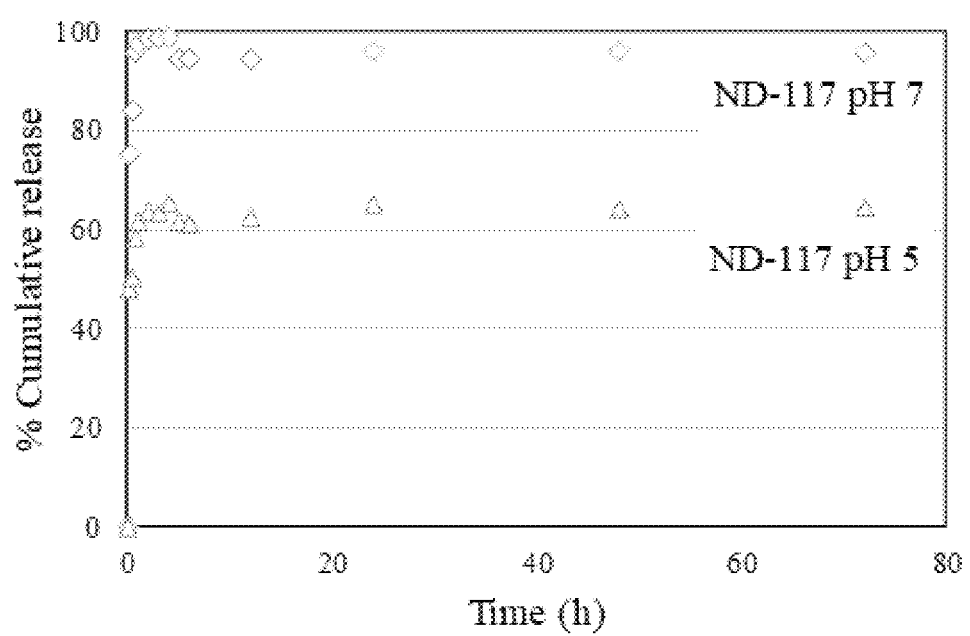
FIG. 8 show the drug release profile of multifunctional multi-functional drug composition capable of pH responsive drug release at two different pH 5.0 and 7.0 and 37° C. for 72 h.
Figure 9:
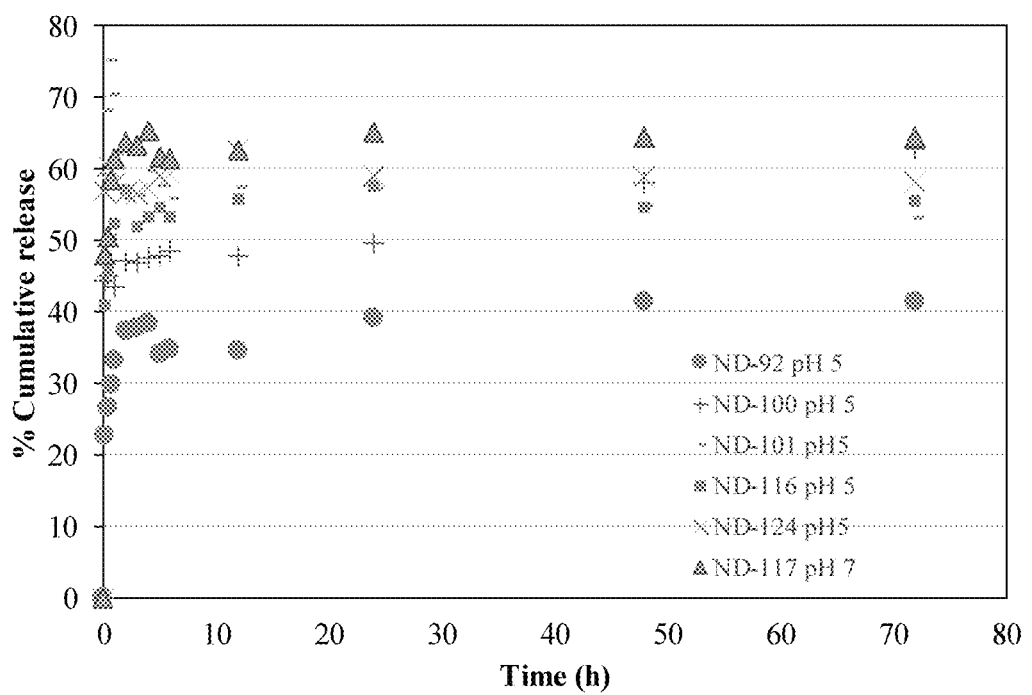
FIG. 9 shows the drug release profile of different nanoformulations at acidic tumour at pH 5.0 and 37° C. for 72 h.
Figure 10:
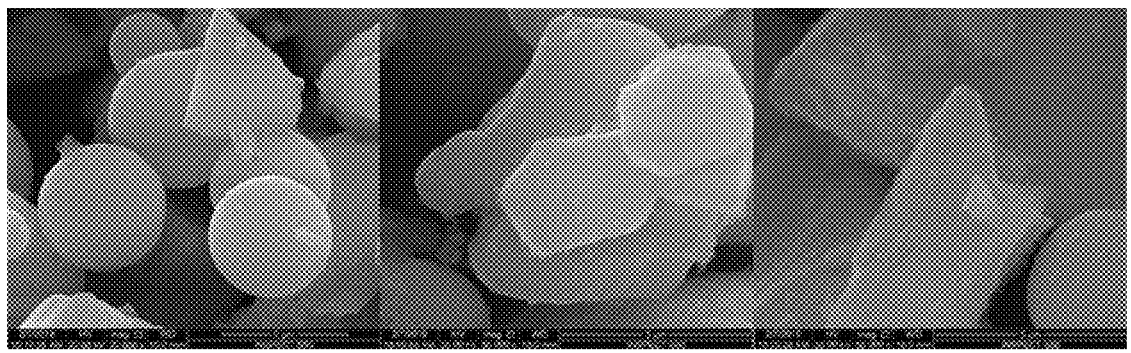
FIG. 10 shows SEM images of: parent silica S-16 (left panel), ND-117, i.e., 10 wt % SPIONs loading over S-16 (center panel) and ND-91, i.e., 10 wt. % iron oxide and 10 wt % nickel oxide loaded over 3D cage type of structured siliceous SBA-16 (right panel).

The drug release profile of multifunctional drug composition capable of pH responsive drug release was subjected to two different pH conditions (pH 5 and 7) at 37° C. for 72 h. A steady drug release trend was observed for 72 h (FIG. 8). The study shows that sample ND-117 shows exemplary drug release capacity at pH 7, while the release modulates with pH variation to pH 5. The observed trend shows that at low pH condition, the release ability of cisplatin is controlled by the electrostatic interactions between cisplatin/S-16 nanoformulation and acidic condition.

Example 11

Scanning electron microscope (SEM) images of 10 wt % iron oxide and 10 wt % nickel oxide loaded over 3D cage type of structured siliceous SBA-16 (ND-91). Parent S-16 was found to be composed of micron sized spherical spheres of about 4 µm. 10 wt % SPIONs loading over S-16 (ND-117) showed no significant changes in the morphological characteristics, which might be due to presence of high surface area. However, in case of ND-91, which involves bimetal oxide species of nickel and iron oxides, some external morphological changes are observed with changes in spherical shaped silica to rectangular shapes.

Example 12

FIGS. 11A-11E show Transmission electron microscope (TEM) images of ND-88, ND-89, ND-90, ND-91 and ND-97, respectively. The TEM analysis showed that dispersion of metal oxides occurs over high surface area of mesopores with particle size ranging between 10-60 nm.

Figure 11A:
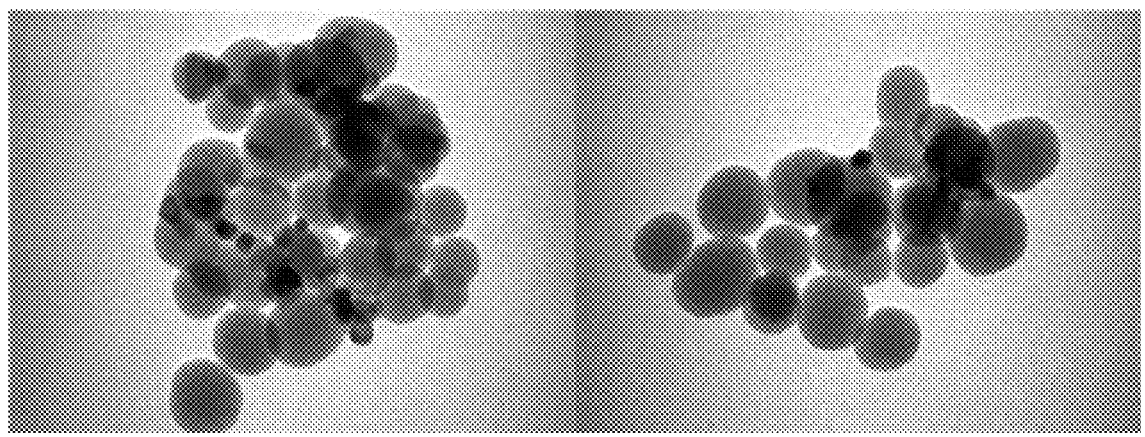
FIG. 11A shows TEM images of 10 wt. % iron oxide loaded over monodisperse hydrophilic spherical silica (ND-88).
Figure 11B:
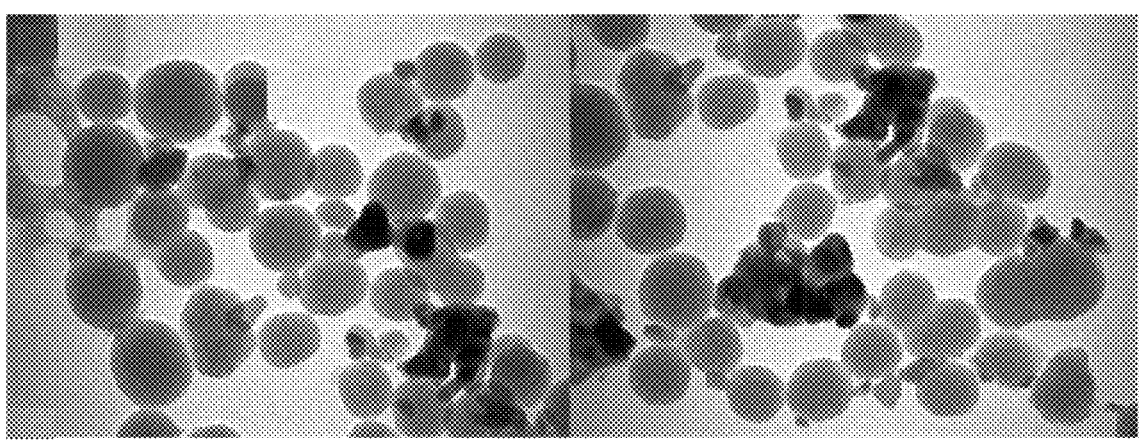
FIG. 11B shows TEM images of 10 wt. % iron oxide loaded over monodisperse hydrophobic spherical silica (ND-89).
Figure 11C:
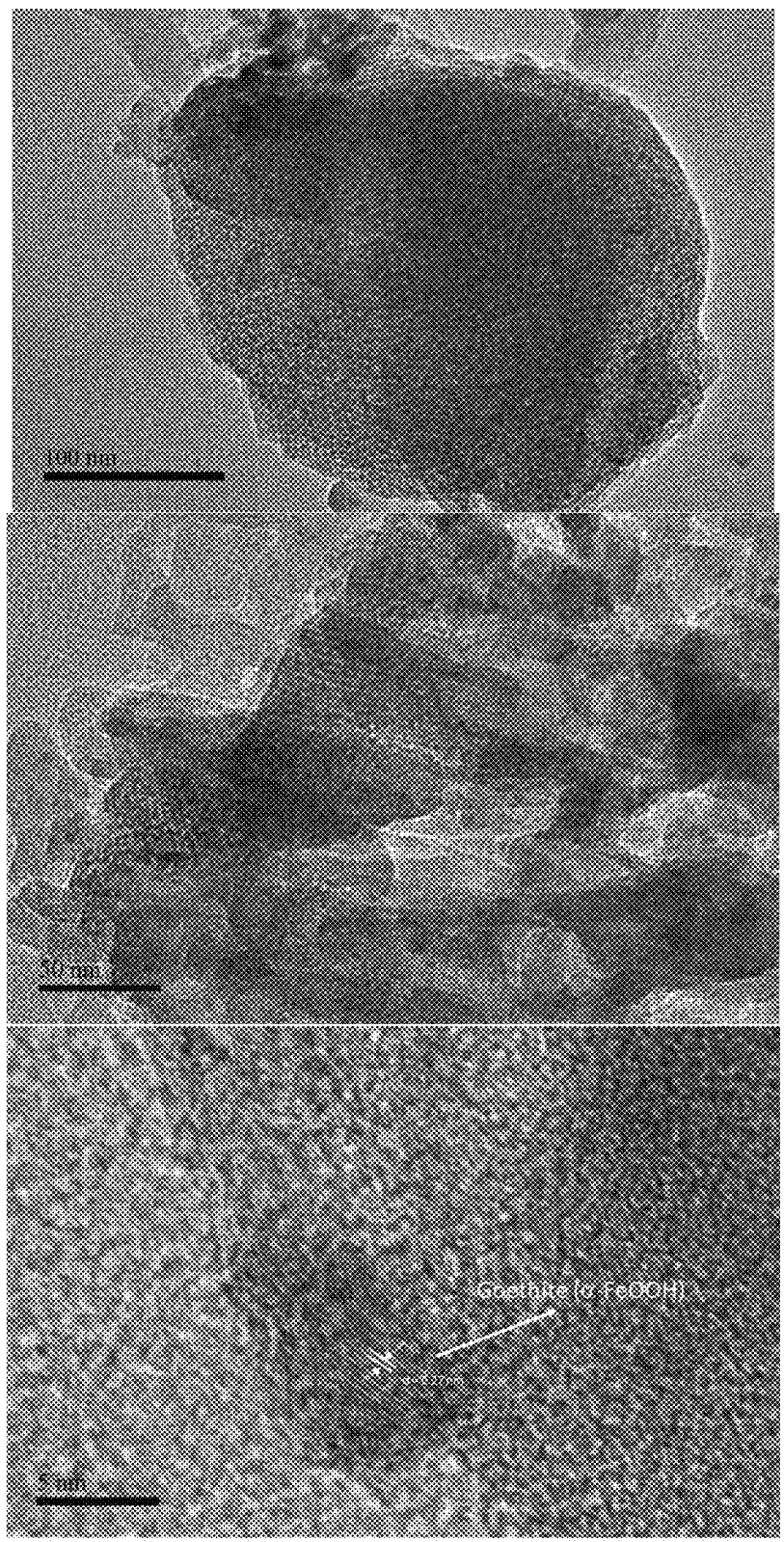
FIG. 11C shows TEM images at three times magnification of 10 wt. % iron oxide and 10 wt. % NiO impregnated over mesosilicalite, in situ designed silicalite-MCM-41 hierarchical porous material (ND-90).

The TEM analysis shows that SPIONs deposition are unique and depends on the support nature, where the dispersion and agglomeration vary based on the nanocarriers pore architecture. FIG. 11A is two TEM images of ND-88 showing iron oxide impregnated over hydrophilic silica at the same magnification (100 nm). The image clearly shows spherical silica balls closely packed and the iron oxide forming nanoclusters (thicker region). A clear external agglomeration of SPIONs as nanosize clusters was observed to be distributed over spheres. Similarly, the TEM image of ND-89 (FIG. 11B) shows SPIONs dispersion over hydrophobic silica. The silica spheres are well separated from each other, while a different types of larger clusters of SPIONs were observed.

ND-90 is the hierarchical mesosilicalite support. The presence of nano sized bimetal oxide species (NiO and SPIONs) are captured over mesosilicalite support (see FIG. 11C). The presence of active iron oxide species contributing to magnetic property has been identified as Goethite (α-FeOOH).

Figure 11D:
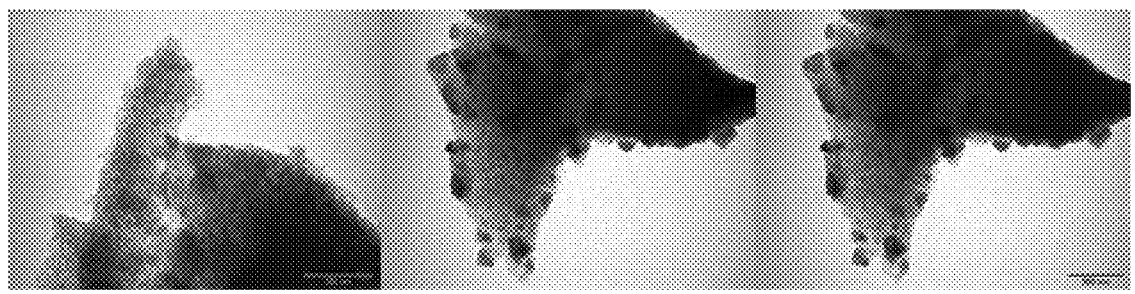
FIG. 11D shows TEM images of 10 wt. % iron oxide and 10 wt % nickel oxide loaded over 3D cage type of structured siliceous SBA-16 (ND-91).
Figure 11E:
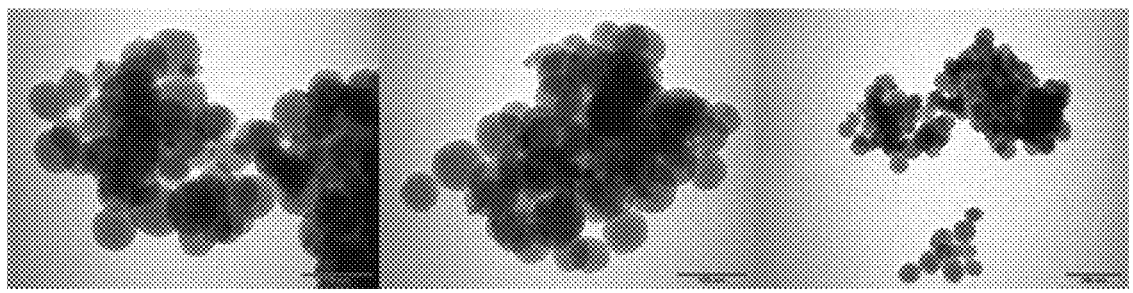
FIG. 11E shows TEM images of 10 wt. % iron oxide loaded over monodisperse hydrophilic spherical silica calcined at 750° C. (ND-97).

The TEM image of the bimetal oxide species impregnated over three-dimensional cage type of SBA-16 pores (ND-91) shows the presence of agglomerated forms of SPIONs as nanoclusters along the pore channels (see FIG. 11D).

ND97 was synthesized using the method used for the synthesis of ND89 using the same hydrophilic silica support and metal content of 10 wt. %. ND-89 calcined at 500° C. for 2 h, while ND-97 calcined at 750° C. In ND-89, dispersed spherical silica was observed, while at high calcination, hydrophobic silica showed aggloromeration effect of metal oxide species, compare FIG. 11B to FIG. 11E.

Example 13

Figure 12A:
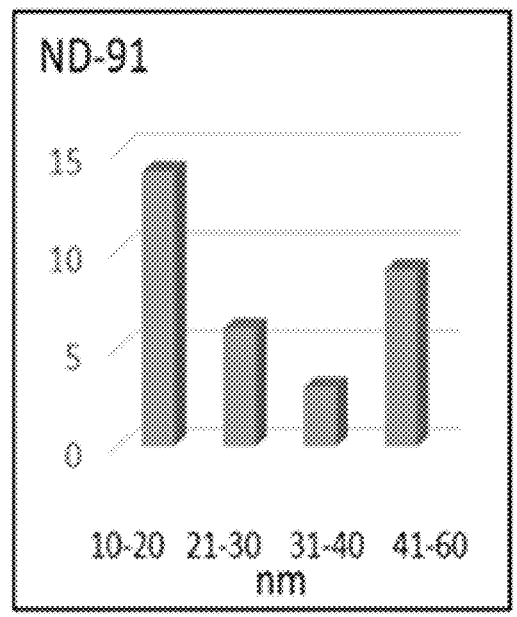
FIG. 12A shows particle size distributions of 10 wt. % iron oxide and 10 wt % nickel oxide loaded over 3D cage type of structured siliceous SBA-16 (ND-91).
Figure 12B:
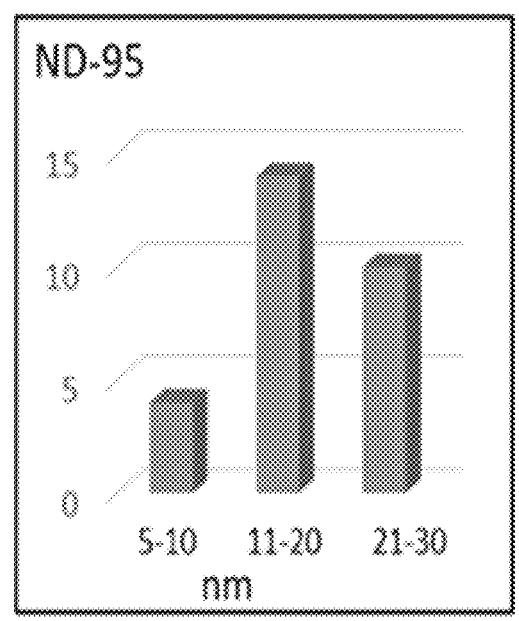
FIG. 12B shows particle size distributions of 10 wt. % Iron oxide loaded over 3D cage type of structured siliceous SBA-16 (ND-95).

Particle size distributions of ND-91, and ND-95 are shown in FIGS. 12A and 12B, respectively. The average SPIONs particle size of the 10 wt % SPIONs/HYPS (ND-88) measured from TEM images was found to be high of about 51.0±1.07 nm, followed by SPIONs/S-16 (ND-95) support in the range of 17±1.83 nm. In SPIONs/MSU-F (ND-51), small sized agglomerated SPIONs in the range of 13±0.92 nm was observed.

Example 14

In-vitro anticancer activity study: Anticancer activity of SPIONs/Silica/APTES/PAA/-cisplatin (ND-117) composite is tested on colon cell line HCT 116 (ATCC® CCL-247™) and breast cancer cell line MCF7, purchased from HyClone, GE Healthcare, Chicago, USA. The cells are grown in RPMI medium with 10% fetal calf serum and 1× penicillin/streptomycin solution purchased from Thermo Fisher, Waltham, USA. The cells were seeded at the rate of 1×104 cells/well of a 96 well plate. None cancerous normal dermal fibroblast primary cells maintained in house are used as a control cell line. After 24 hours of culture at 37° C., 95% relative humidity and 5% CO₂ levels, cells are treated with varied concentration of ND-117 along with the solvent in which the drugs are solubilized. Upon further culture for another 48 hours, the cells are subjected to end point cell survival assay using MTT (3-(4,5-dimethylthiazol-2-yl)-2,5-diphenyltetrazolium bromide) dye reduction test.

MTT Assay: To each of the drug treated and control 96 culture wells, 20 µl of 10 mg/ml MTT was added and incubated for up to 24 hours under the same culturing conditions described above. The wells were washed off the unbound dye using ample amounts of PBS (Phosphate buffered saline: Thermo Fisher, Waltham, USA). The formazan dye formed was solubilized by adding 150 µl of 0.1% NP40 in isopropanol (MTT solvent) and shaken on a plate shaker for 15 mins. The optical density (OD) of the solubilized dye was read at 590 nm using a multiplate reader (Tecan Infinite® 200 PRO, Tecan Trading AG, Switzerland). The OD was compared and calculated against control and expressed as percentage of cell survival.

In vitro MTT assay is a useful tool to study the safety of anticancer drugs and to determine the effective dose for new drug therapy. A good drug candidate should be effective in killing the cancer cells, while exerting negligible toxicity on normal cells.

The invention claimed is:

1. A multi-functional drug composition capable of pH responsive drug release, comprising:
   cisplatin,
   functionalized SBA-16 mesoporous silica nanoparticles,
   superparamagnetic iron oxide nanoparticles (SPIONs) or a mixture of SPIONs and NiO nanoparticles, and
   polyacrylic acid,
   wherein the SPIONS are present in the pores of the functionalized SBA-16 mesoporous silica nanoparticles and the functionalized SBA-16 mesoporous silica nanoparticles are functionalized with 3-aminopropyl-triethoxysilane, and
   wherein the functionalized SBA-16 mesoporous silica nanoparticles containing the SPIONs are encapsulated with the polyacrylic acid and the polyacrylic acid is bonded to the functionalized SBA-16 mesoporous silica nanoparticles with an amide bond.

2. The multi-functional drug composition of claim 1, wherein the functionalized SBA-16 mesoporous silica nanoparticles have pore sizes in the range of 1 nm to 60 nm.

3. The multi-functional drug composition of claim 1, wherein the functionalized SBA-16 mesoporous silica nanoparticles have a surface area in the range of 400 to about 1400 $m^2/g$.

4. The multi-functional drug composition of claim 1, wherein the functionalized SBA-16 mesoporous silica nanoparticles have a pore volume in the range of 0.30-0.90 mL/g.

5. The multi-functional drug composition of claim 1, wherein the cisplatin is present in amount in the range of 0.001 to 1.8 mmol/g of the total weight of the multi-functional drug composition.

6. A pharmaceutical composition comprising the multi-functional anticancer composition of claim 1.

7. The pharmaceutical composition of claim 6, further comprising one or more carriers and/or excipients selected from the group consisting of a buffer, an inorganic salt, a fatty acid, a vegetable oil, a synthetic fatty ester, a surfactant, a sugar, a polymer, and combinations thereof.

* * * * *

UNITED STATES PATENT AND TRADEMARK OFFICE
CERTIFICATE OF CORRECTION

PATENT NO. : 11,160,763 B2
APPLICATION NO. : 16/295655
DATED : November 2, 2021
INVENTOR(S) : Balasamy Rabindran Jermy et al.

It is certified that error appears in the above-identified patent and that said Letters Patent is hereby corrected as shown below:

On the Title Page

Item (71), Applicant's Name is incorrect.
Item (71) should read: Imam Abdulrahman Bin Faisal University, Dammam (SA)

Item (73), Assignee's Name is incorrect.
Item (73) should read: Imam Abdulrahman Bin Faisal University, Dammam (SA)

Signed and Sealed this
Twenty-fourth Day of January, 2023

Katherine Kelly Vidal
*Director of the United States Patent and Trademark Office*